United States Patent [19]
Biessen et al.

[11] Patent Number: 5,885,968
[45] Date of Patent: Mar. 23, 1999

[54] TRIANTENNARY CLUSTER GLYCOSIDES, THEIR PREPARATION AND USE

[75] Inventors: Ericus Anna Leonardus Biessen, Leiden; Theodorus Josephus Cornelis van Berkel, Haarlem; Jacobus Hubertus van Boom, Voorschoten, all of Netherlands

[73] Assignees: Rijksuniversiteit te Leiden, AV Leiden; Nederlandse Hartstichting, The Hague, both of Netherlands

[21] Appl. No.: 382,022

[22] PCT Filed: Aug. 11, 1993

[86] PCT No.: PCT/NL93/00169

§ 371 Date: May 4, 1995

§ 102(e) Date: May 4, 1995

[87] PCT Pub. No.: WO94/04545

PCT Pub. Date: Mar. 3, 1994

[30] Foreign Application Priority Data

Aug. 11, 1992 [NL] Netherlands ............... 9201440

[51] Int. Cl.$^6$ ............... A61K 31/70; C07H 15/00
[52] U.S. Cl. ............... 514/25; 536/4.1; 536/17.2; 536/17.3
[58] Field of Search ............... 536/4.1, 17.2, 536/17.3; 514/25

[56] References Cited

U.S. PATENT DOCUMENTS 4,751,219  6/1988  Kemper ............... 514/26

*Primary Examiner*—Elli Peselev
*Attorney, Agent, or Firm*—Hoffmann & Baron, LLP

[57] ABSTRACT

Triantennary cluster glycoside, wherein each glycoside residue is attached to the branching point of the cluster by a spacer of a long, flexible, hydrophilic chain comprising at least 4 atoms in the chain. The glyciside spacer preferably comprises at least two hydrophilic groups. Use of the triantennary cluster glycoside in pharmaceutical preparations, for instance hypolipidemic medicines.

23 Claims, 16 Drawing Sheets

FIG. 9

$$\begin{cases}
[GO-X^1-]_3A-X^2-Z & (1)\\
-(CHR^1)_n[O(CHR^2)_p]_rOCH_2O(CHR^3)_q- & (2)\\
-NH[CO(CHR^4)_sNH]_vCO(CHR^5)_tCO[NH(CHR^6)_uCO]_w- & (3)\\
[GO-(CH_2CH_2O)_4CH_2O(CH_2)_q-]_3CNHCOCH_2NHCO(CH_2)_4CONHCHCH_2CO-Ochol & (4)\\
[GO-(CHR^2)_p]_rOCH_2O(CHR^3)_q-]_3C-X^2-Z & (5)\\
G'O-(CHR^1)_n[O(CHR^2)_p]_rOH & (6)\\
[CH_3SCH_2O(CHR^3)_q-]_3C-X^2-Z' & (7)\\
[GO-(CHR^1)_n[O(CHR^2)_p]_rOCH_2O(CHR^3)_q-]_3C-NH-X^3-Z & (8)\\
[CH_3SCH_2O(CHR^3)_q-]_3C-NHQ & (9)\\
G'-SC_2H_5 & (10)\\
HO(CHR^1)_n[O(CHR2)_p]_rOH & (11)\\
(ROCH_2-)_3C-NHCOCH_2NHQ^1 & (13)\\
[(RO(CH_2)_3-]_3C-R' & (16)
\end{cases}$$

FIG. 10
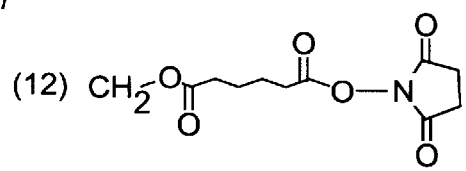
(12)
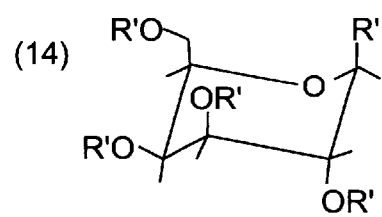
(14)
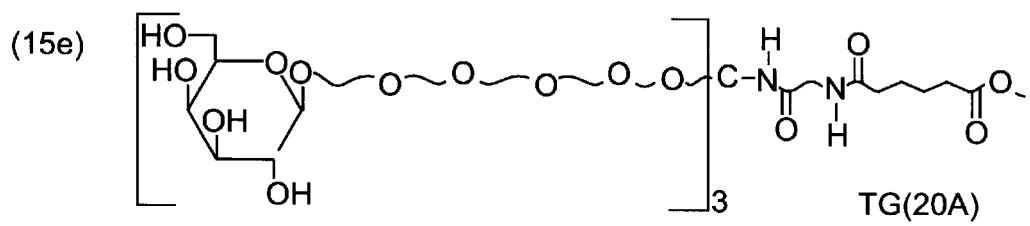
(15e) TG(20A)
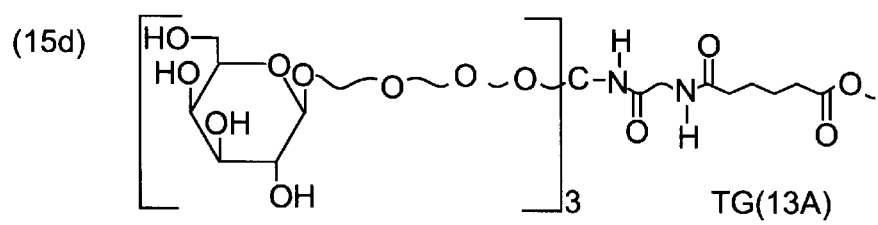
(15d) TG(13A)
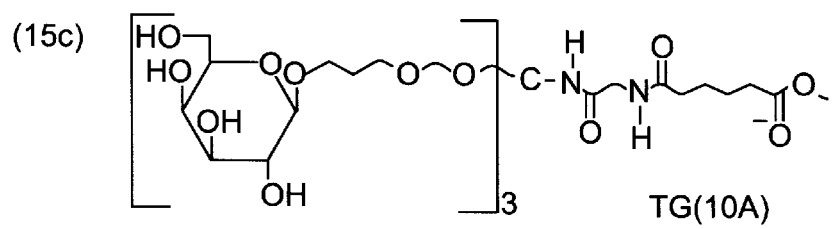
(15c) TG(10A)
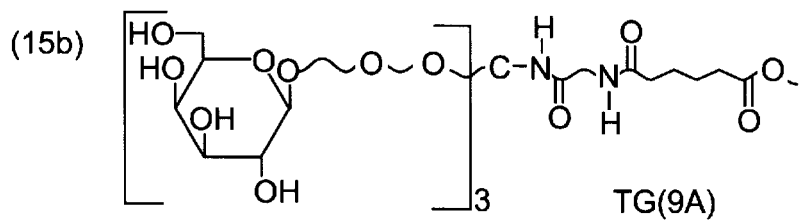
(15b) TG(9A)
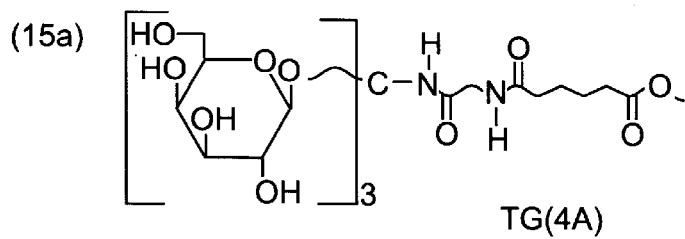
(15a) TG(4A)

(23)

TRIANTENNARY CLUSTER GLYCOSIDES, THEIR PREPARATION AND USE

FIELD OF THE INVENTION

This invention relates to triantennary cluster glycosides, i.e., compounds which contain a cluster of three sugar groups and thereby can be recognized by certain receptors present in the human or animal liver.

Such triantennary cluster glycosides can be used for different purposes, for instance, if the triantennary cluster glycoside comprises a cholesterol residue or an alternative lipophilic group, for the in vivo delivery of lipoproteins and lipid vesicles from the blood to the liver within the framework of a therapeutic treatment of hyperlipidemia.

PRIOR ART

Ways of piloting lipoproteins and lipid vesicles to the liver via a suitable route have been searched for before, on the one hand to create a transport vehicle that directs drugs specifically to the liver and, on the other hand, to remove the atherogenic low density lipoprotein (LDL) from the bloodstream.

Glycolipids have been developed in order to induce liver uptake of lipid vesicles or lipoproteins via the asialoglycoprotein receptor on the parenchymal cell of the liver, such as cholesteryl glycosides (refs. 1–4) lactosyl cerebrosides and gangliosides (refs. 5–9) and chemically modified phospholipids (refs. 10–11).

However, when associated to lipoproteins/liposomes, these known compounds will display preference for uptake by the likewise galactose recognizing fucose/galactose receptor on hepatic Kupffer cells, which hampers a potential application of these compounds in drug-targeting. The fucose/galactose receptor binds sugars, glycoproteins and particles, exposing a high density of terminal galactose groups (ref.22). Probably, high affinity binding does not essentially require di-, tri- or tetraantennarity of the glycoside.

The afore-mentioned glycolipids contain a ligand which is recognized by the asialoglycoprotein receptor on the parenchymal cell of the liver. This receptor represents an uptake system of high capacity and a unique localization on the parenchymal cell of the liver. The receptor can recognize sugars and glycoproteins with terminal galactose groups, it having a clear preference for oligoantennary sugars.

The above-mentioned compounds further comprise a structure which provides for an association of the ligand to lipid vesicles or lipoproteins. To that end, the substances are provided with a lipid part which associates spontaneously with lipid vesicles or lipoproteins.

A disadvantage of these known glycolipids is inter alia that they are not water-soluble, which makes the in vivo use of these substances difficult.

For this reason research has been conducted on a water-soluble clustered galactosolipid: tris-gal-chol of formula 22 (refs. 12–15, and 26). These investigations demonstrated that this compound is capable of irreversibly removing cholesterol from the bloodstream and inducing cholesterol uptake by the liver.

However, various disadvantages are associated with the use of tris-gal-chol as a hypolipidemic agent. In the first place, its potency is low: high doses of tris-gal-chol are necessary for a significant reduction of the LDL level in the bloodstream (ref. 15). Moreover, after injection of tris-gal-chol, the LDL is not removed via the asialoglycoprotein receptors on hepatocytes but via the Fuc/Gal receptors on hepatic Kupffer cells. Removal by the first-mentioned type of cells is much to be preferred to a removal by the last-mentioned type of cells, since only hepatocytes are capable of converting cholesterol from LDL into bile acids and secreting them in the bile.

It can be argued that both the low specificity for targeting (lipo)proteins to the hepatic parenchymal cell and the low hypocholesterolemic potency of tris-gal-chol were linked up with the low specificity and affinity of the glycoside for the asialoglycoprotein receptor. A further optimization of cluster glycoside from tris-gal-chol with respect to the affinity and specificity for the asialoglycoprotein receptor were required.

Previously, Lee et al. had reported a study of the prerequisites of high affinity recognition by the asialoglycoprotein receptor (ref.24). More in particular, a study on the affinity of three types of cluster glycosides was described: 1) synthetic branched oligosaccharide structures; 2) tris-gal/tris-lac dendrites and oligomers thereof wherein the terminal sugar moiety is directly attached to the branching point of the cluster glycoside; and 3) glycopeptide derivatives. From binding studies and modelling studies using the Fisher-Hirschfelder-Taylor model it appeared that besides the valency of the cluster galactoside there are other affinity determinants for the asialoglycoprotein receptor. Given a certain valency, the maximum spatial intergalactose distances and the flexibility of the arm connecting the galactose residues at the branching points also affected the affinity for this receptor.

Applying these basic rules, they have synthesized the above mentioned compounds, and esp. tri-, tetra- and hexavalent glycosides, and have determined the affinity of these cluster glycosides.

However, some of the conclusions or results from this rather theoretical study are highly questionable. Firstly, only a first indication of a "maximum" spatial distance of the galactose residues is obtained, because the model used does not take into account any restrictions imposed to the examined structures by physical effects such as e.g. hydrofobicity, hydratation and sterical hindrance.

Secondly, the flexibility of the suggested arm connecting the sugar moieties to the branching point, e.g. of the rather hydrophobic aminohexyl chain, is strongly overestimated. Hydrophobic spacers tend to aggregate with other hydrophobic structures or internally. In addition, in an aqueous environment an isolated hydrophobic spacer is surrounded by a rather rigid water structure that limits the flexibility of the spacer.

In the binding assay used to determine the affinity of the cluster glycosides examined, Lee et al. find affinities which are unrealistically high. For instance, they find affinities for 4 ligands, viz. ASOR, $Lac_{40}BSA$, tris(gal)AHT and Asp(tris(Lac)AHT)$_2$, of respectively 0.5, 0.25, 8,000 and 45 nM. The 4 ligands mentioned were also tested by others (refs 23 and 25). The affinities measured by these others as well as by the present inventors are usually about 5, 15, 400,000 and 6,500 nM respectively. These more realistic values are at least 10–50 times higher than the values claimed by Lee et al., which means that the real affinity for the receptor is at least 10–50 times lower.

Based on these facts, it is justified to compare the relative gain in affinity of the cluster glycosides towards ASOR or tris(gal)AHT (monomer tris(gal) in ref 23 or TG(4 Å) in the present description) instead of comparing the absolute affinities. The results claimed by Lee et al. correspond to a gain in affinity with a factor of about 80–160 for trivalent cluster galactosides upto a factor of about 600 for hexavalent cluster galactosides as compared to tris(gal), which is a close analogue of TG(4 Å) and identical to the monovalent cluster glycoside developed by Mary et al (ref.23).

According to the present invention it has been found that the maximal gain in affinity and, in particular, specificity towards the asialoglycoprotein receptor, as obtained by Lee et al for trivalent cluster glycosides, could still be subject to considerable improvement. This is highly desirable in view of the aimed application in cholesterol lowering and/or hepatotrophic drug-targeting.

BRIEF SUMMARY OF THE INVENTION

The present invention relates to the introduction of long, flexible, hydrophilic and often hydratable chains or spacers in triantennary or trivalent cluster glycosides, which chains connect the sugar groups of the cluster glycoside with the branching point of the cluster. For cluster glycosides with terminal galactose groups, the introduction of such a chain results in a markedly increased affinity and, even more important, specificity, for the galactose-specific asialoglycoprotein receptors on the hepatic parenchymal cells.

In the present description, the term "long" refers to a spacer of at least 10 Å, and preferably of up to 20 Å or larger. A "hydrophilic" spacer is a spacer which consists essentially of units of branched or straight $C_1$–$C_4$ alkylene groups, esp. ethylene and propylene groups, arranged between two hydrophilic groups, such as oxo, thio, amino, amide or ureido groups. Schematically, such spacers may be represented by e.g. the formula —[—HG-Alk-]$_e$—, wherein the groups HG independently represent a hydrophilic group, the groups Alk independently represent an afore-defined alkylene group, and e normally varies from 1–8, preferably from 1–4. Flexible chains preferably do not contain double and triple bonds and are preferably hydrophilic. Finally, "hydratable" groups generally comprise both hydrogen bridge donors and acceptors. Such groups are capable to cluster water molecules around the chain.

By way of illustration, an elongation of a flexible, hydrophilic and hydratable chain according to the invention, e.g. a chain consisting of oligo ethylene glycol units, for a triantennary galactoside from 3.7 to 19.5 Å increases its affinity for the asialoglycoprotein receptor by a factor of 2,000. The affinity for the fucose/galactose recepter on the Kupffer cell, on the other hand, remains constant upon elongation of this chain from 3.7 to 19.5 Å.

A cluster glycoside with an increased affinity and specificity for the asialoglycoprotein receptor can, after being coupled to a lipid to form a glycolipid, be used for effecting an increased uptake of lipoproteins and lipid vesicles by the parenchymal liver cells. This accordingly offers perspectives for the development of both an effective hypolipidemic medicine and a parenchymal liver cell-specific drug carrier.

BRIEF DESCRIPTION OF THE DRAWINGS

FIG. 9 depicts Formulas 1–11, 13 and 16.

FIG. 10 depicts Formulas 12, 14 and 15a–e.

DETAILED DESCRIPTION OF THE INVENTION

Figure 1:
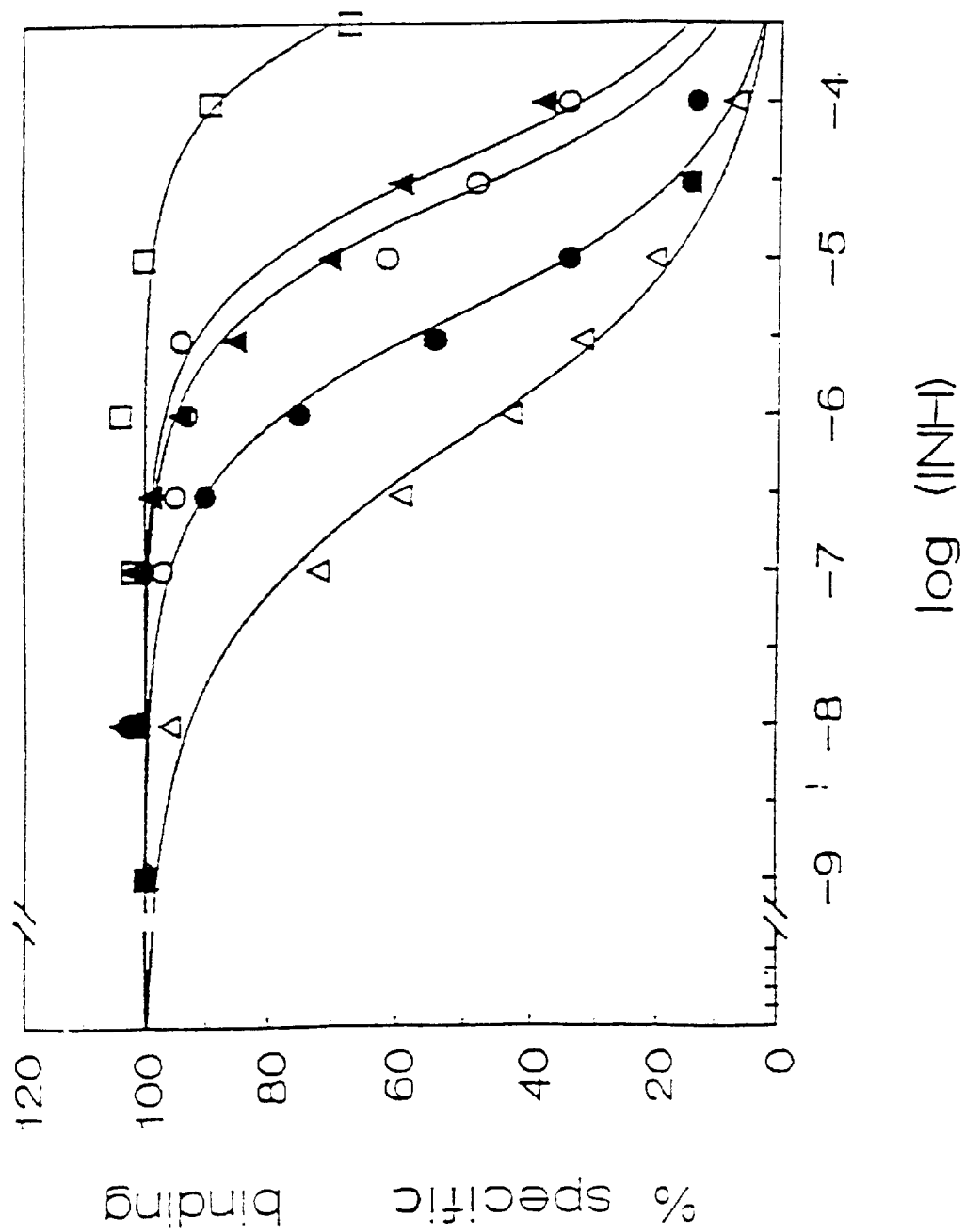
FIG. 1 illustrates the result of increasing of the length of glycoside spacers.

The present invention provides a triantennary cluster glycoside having the formula 1:

$$[GO\text{—}X^1\text{—}]_3A\text{—}X^2\text{—}Z \qquad (1)$$

wherein each glycoside GO is attached to the branching point A by a long, flexible, hydrophilic spacer $X^1$ which spacer comprises at least 4 atoms in the chain and consists essentially of units of branched or straight $C_1$–$C_4$ alkylene groups arranged between two hydrophilic groups, represented by the formula:

—[HG-Alk-]$_e$— wherein the groups HG independently represent a hydrophilic group, wherein the groups Alk independently represent a branched or straight $C_1$–$C_4$ alkylene group, and wherein e varies from 1–8, wherein $X^2$ is an end group spacer of a chain length of at least 4 atoms in the chain and Z is an end group being chosen from an optionally protected reactive group, a lipophilic group, a drug residue and a drug carrier residue, with the exclusion of tetrakis-O-(3-carboxypropionyl)pentaerythritol tetrakis-(1,2,3,4-tetra-O-benzyl-α-D-glucopyranosid-6-yl)tetraester and tetrakis-O-(3-carboxy-propionyl)pentaerythritol tetrakis-(α-D-glucopyranosid-6-yl)tetraester.

The present invention further provides a use of the present new compounds, viz., a pharmaceutical preparation comprising a triantennary cluster glycoside according to the present invention, as well as at least one pharmaceutically acceptable carrier.

Preferably, the chain length of the glycoside spacer is longer than 4 atoms in the chain, such as 8 or more, or even 10 or more atoms in the chain. It is here preferred that the chain of the glycoside spacer comprises at least two hydrophilic groups. Although in principle any hydrophilic group is eligible, the hydrophilic group is preferably chosen from —O—, —CO—, —NH—, —CONH—, —NHCO—, —S—, —N(CH$_3$)CO—, and CON(CH$_3$)—. Although —OCO— and —COO— groups may also be used, these groups are less preferred due to their sensitivity to hydrolysis. The biological stability of the triantennary compounds according to the invention can be markedly improved by substituting the methyl acetate (O—C—O) by a methyl thio acetal or ethylene glycol ether, by substituting the amide by methylamide and esters by thioesters, thioethers or ethers.

Very suitable is a triantennary cluster glycoside in which the glycoside spacer satisfies the formula 2:

$$\text{—}(CHR^1)_n[O(CHR^2)_p]_rOCH_2O(CHR^3)_q\text{—} \qquad (2)$$

wherein $R^1$, $R^2$ and $R^3$ independently represent a hydrogen atom or a methyl group, p, and q independently represent an integer from 1–4, and n, and r represent an integer from 0–6.

It is preferred that $R^1$, $R^2$ and $R^3$ each represent hydrogen atom, and that n is an integer from 0–4, p is an integer from 2–3, q is an integer from 1–3 and r is an integer from 1–5.

Although the glycoside residues (sugar residues) can in principle be freely chosen, they are preferably chosen from a β-D-lactosyl group and monosaccharides having a high intrinsic affinity for the asialoglycoprotein receptor, including β-D-galactosyl, 2-acetamido-2-deoxy-galactopyranosyl, 1-phenyl-β-D-galactosyl, 1-propyl-β-D-galactosyl or 1-butyl-β-D-galactosyl.

In a particular embodiment of a triantennary cluster glycoside according to the invention, an end group spacer having a chain length of at least 4 atoms in the chain is attached to a carbon atom being the branching point of the cluster.

Here, too, the chain length is preferably longer than 4 atoms in the chain, such as at least 6, preferably at least 8 or even 10 or more atoms in the chain. It is preferred that the chain of the end group spacer comprises at least one alkylene group and at least two hydrophilic groups, wherein the hydrophilic group is preferably chosen from —O—, —CO—, —NH—, —S—, —CONH—, —NHCO—, —C(O)S—, —CON(CH$_3$)— and —N(CH$_3$)CO—.

Very suitable is a triantennary cluster glycoside in which the end group spacer satisfies the formula 3:

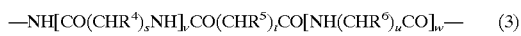

wherein $R^4$, $R^5$ and $R^6$ independently represent a hydrogen atom or an alkyl group having 1–4 carbon atoms, s, t and u independently represent an integer from 1–4, and v and w independently represent an integer from 0–4.

It is preferred that $R^4$, $R^5$ and $R^6$ each represent a hydrogen atom, and that v is an integer from 1–2, w is an integer from 0–2 and s, t and u independently represent an integer from 1–4.

In a particularly preferred embodiment of a triantennary cluster glycoside according to the invention, the end group spacer has an end group attached to it, chosen from an optionally protected reactive group, a lipophilic group, a drug residue and a drug carrier residue. Preferably, the end group comprises a hydroxy group, an alkoxy group having 1–4 carbon atoms, an amino group, a 3β-cholestrol residue, a N$_\alpha$,N$_\epsilon$-dioleoyl lysine residue, a 5β-cholanic acid-3α-ol oleate residue, a 5-cholenic acid-3β-ol oleate residue, a 5β-cholanic acid-3α,12α-diol dioleate residue, or a lipoprotein residue, but above all a cholesterol residue.

A suitable triantennary cluster glycoside according to the invention can be represented by formula 1:

$$[GO—X^1—]_3A—X^2—Z \quad (1)$$

wherein GO— represents the glycoside residue, $X^1$ the glycoside spacer, $X^2$ the end group spacer and Z the end group.

It is not necessary that the branching point A is a carbon atom. The branching point can also be a group, such as a sugar group, e.g. a glucose group.

A particularly preferred triantennary cluster glycoside according to the invention satisfies the formula 4:

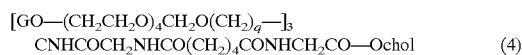

wherein q is an integer from 1–3, GO— represents a galactose residue and —Ochol represents a cholesterol residue.

The cluster glycoside according to the invention is distinguished from the known cluster glycosides by the property that the sugar group is attached to the branching point of the cluster through a flexible, hydrophilic chain ($X^1$), which may be made up of an alkylene diol which may or may not be elongated by an oligomeric chain of units of ethylene glycol or propylene glycol. In its turn, the branching point is attached to the end group Z, whose composition depends on the final application contemplated, via a peptide-like chain ($X^2$) preferably 10–15 Å long.

The sugar group consists preferably of a galactosyl, a 2-acetamido-2-deoxy-β-D-galactopyranosyl, a 1-phenyl-galactopyranosyl, a 1-propyl-galactopyranosyl, a 1-butyl-galactopyranosyl, or a lactosyl group. These galactosyl units display a high intrinsic affinity for the galactose binding site on the asialoglycoprotein receptor. The described cluster galactosides in question have as an advantage over the cluster glycoside component of the previously described tris-gal-chol that their affinity and specificity for the asialoglycoprotein receptor is much higher (up to a factor 2,000).

The observed increase in affinity of TG(20 Å)—a cluster glycoside according to the invention (see FIG. 15e:

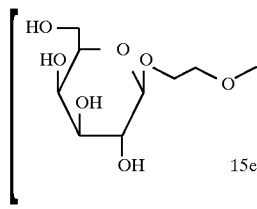 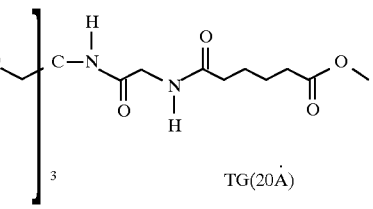

and the examples)—induced by elongation of the spacer using a flexible and hydrophilic chain of 19.5 Å (of at least 4 C-atoms), being 2000 fold as compared to TG(4 Å)=tris (gal), is considerably larger than that realized by Lee et al (ref.24) for asp (tris (Lac)AHT)$_2$ as compared to tris(gal) (170–670 fold). This is partly due to the fact that the spacer of TG(20 Å), connecting the glycoside with the branching point of the dendrite is highly flexible and hydrophilic. The high hydrophilicity of the spacer enables optimal hydratation and flexibility of the spacer in aqueous solution. Lee et al. (ref.24) and Mary et al.(ref.23) apply a hydrophobic hexyl moiety for elongating the spacer, which probably results in sub-optimal spread and flexibility of the triantennary structure in aqueous solution.

When a glycolipid of a high hypolipidemic potency is contemplated, then the end group Z comprises a strongly lipophilic group such as 3β-cholesterol, N$_\alpha$,N$_\beta$-dioleoyl lysine, 5β-cholanic acid-3α-ol oleate, 5-cholenic acid-3β-ol oleate, 5β-cholanic acid-3α,12α-diol dioleate. As a consequence of the high affinity of the cluster glycoside component for the asialoglycoprotein receptor, the hypolipidemic potency of this glycolipid is very high and the uptake of lipid vesicles or lipoproteins by the hepatic parenchymal cell is strongly promoted.

When it is intended for the cluster glycoside structure to be used for directing antisense DNA to the liver parenchymal cell, then the end group Z comprises an oligonucleotide chain which is coupled to the $X^2$ group of the cluster glycoside through the free phosphate group at the 5' end via an acid-labile phenol ester or phosphamide band. By directing antisense DNA to the liver, it is possible to accomplish an inhibition of the biosynthesis of an undesired gene product.

If antisense inhibition of the synthesis of the highly atherogenic lipoprotein (a) [lp(a)] is contemplated, then the end group Z could comprise the base pair sequence 5'-CGTCGTGGACTGTTTCG. This sequence binds extremely specifically to the mRNA which codes for the apolipoprotein(a), the protein component of lp(a).

When an antisense inhibition of the replication of the hepatitis B virus is aimed for, then the end group Z comprises the base pair sequence 5'-GTTCTCCATGTTCGG. This sequence recognizes extremely specifically the mRNA which codes for the hepatitis B virus antigen (ref. 21).

When it is intended for the cluster glycoside structure to be used for directing antiviral agents to the liver, and more in particular to the parenchymal liver cells, the end group Z comprises a compound with antiviral activity. Coupling an antiviral therapeutic to group $X^2$ can be effected via an acid-labile phosphamide band.

Possible antiviral agents which are eligible for derivatization with the cluster glycoside are: 5-(2-bromovinyl)-2'-deoxyurdine and 2'-fluoroarabinofuranosyl-5-iodo cytosine, both potent inhibitors of the hepatitis B DNA polymerase. These compounds can after phosphorylation be coupled to the hydroxyl group of tyrosine ($X^2$) or the free ε-amino group of lysine ($X^2$).

As a therapeutic against Leishmaniasis, primaquine could be considered, which, via its free carboxyl groups, which are not essential to its activity, can simply be coupled to $X^2$ of the glycoside.

The triantennary cluster glycosides according to the invention can be prepared by methods which are known per se. The preparation of the new triantennary cluster glycosides is a subject that is included by the invention.

The present invention provides, for instance, a method for preparing a triantennary cluster glycoside of the formula 5:

wherein GO— is a glycoside residue, $X^2$ is an end spacer, Z is an end group, $R^1$–$R^3$ independently represent a hydrogen atom or an alkyl group having 1–4 carbon atoms, p and q independently represent an integer from 1–4 and n and r represent an integer from 0–6, in which method a compound of the formula 6:

wherein G'O— represents the residue of a protected glycoside, is reacted with a compound of the formula 7:

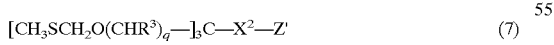

wherein Z' stands for the end group Z or a group to be replaced by the end group Z, the group Z' is the compound obtained, if it represents a group to be replaced by the end group Z, is replaced by the end group Z and previously or subsequently the glycoside residues of the compound obtained are de-protected.

The reaction of the compound of the formula 6:

with the compound of formula 7:

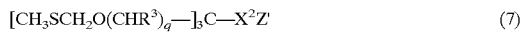

is preferably carried out in the presence of N-iodosuccinimide and trifluoromethanesulfonic acid.

During the reaction, the glycoside residues are protected, for instance by hydroxyl-protecting benzoyl groups, which can be removed later by treatment with potassium tert. butylate.

In this method, Z' in the formula 7:

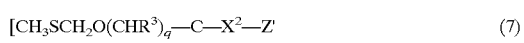

can for instance be a protected reactive group which, after de-protection, is replaced by an end group Z, chosen from a lipophilic group, a drug residue and a drug carrier residue.

The invention also provides a method for preparing a triantennary cluster glycoside of the formula 8:

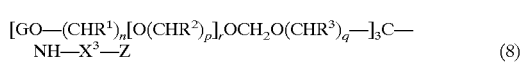

wherein GO— is a gylcoside residue, Z is an end group, $R^1$–$R^3$ independently represent a hydrogen atom or an alkyl group having 1–4 carbon atoms, p and q independently represent an integer from 1–4, n and r represent an integer from 0–6 and $X^3$ represents an end group spacer, in which method a compound of the formula 6:

wherein G'— represents the residue of a protected glucoside, is reacted with a compound of the formula 9:

wherein Q stands for an amino-protecting group, the amino group in the compound obtained is de-protected and the free amino group thereby obtained is converted into a group —NH—$X^3$—Z, and previously or subsequently the glycoside residues of the compound obtained are de-protected.

The compound of the formula 6:

which is used as starting material in these methods, is preferably prepared by reacting a compound of the formula 10:

with a compound of the formula 11:

The reaction of the compound of the formula 10:

with the compound of the formula 11:

is preferably carried out in the presence of N-iodosuccinimide and trifluoromethanesulfonic acid.

An example of a method according to the invention is a method comprising the following steps:

a) 1-Methyl-6-succinimidyl adipate (formula 12):

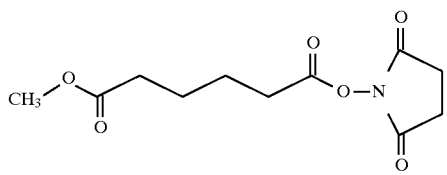

is prepared in a manner that is known per se from 1-methyladipic acid by reaction with N-hydroxysuccinimide in the presence of N,N'-dicyclohexylcarbodiimide.

b) N-(2-hydroxy-1,1-bis(hydroxymethyl)ethyl)-glycinamide (formula 13:

$$(ROCH_2—)_3C—NHCOCH_2NHQ^1 \qquad (13)$$

wherein R=H and $Q^1$=H) is prepared in a manner known per se by a reaction of 2-amino-2-hydroxy-methyl-1,3-propanediol with benzyloxycarbonyl glycine in the presence of N,N'-dicyclohexylcarbodiimide, whereafter the protecting benzyloxycarbonyl group is removed in a manner known per se by reaction with $H_2$ in the presence of Pd/carbon as catalyst.

c) N-(2-hydroxy-1,1-bis(hydroxymethyl)ethyl)-$N^\alpha$-(1-(6-methyl)-adipyl)glycinamide (formula 13: $(ROCH_2—)_3$ C—NHCOCH$_2$NHQ$^1$, wherein R=H and $Q^1$=—CO(CH$_2$)$_4$COOCH$_3$) is prepared in a manner known per se by a reaction of the compound obtained under (b) with the 1-methyl-6-succinimidyl adipate obtained under (a).

d) N-[tris[[(methylthiomethyl)oxy]methyl]methyl]-$N^\alpha$-(1-(6-methyl)adipyl)glycinamide (formula 13: $(ROCH_2—)_3C—NHCOCH_2NHQ^1$, wherein R=—CH$_2$SCH$_3$ and $Q^1$=—CO(CH$_2$)$_4$COOCH$_3$) is prepared in a manner known per se by a reaction of the compound obtained under (c) with dimethyl sulfide in the presence of benzoyl peroxide.

e) Ethyl 2,3,4,6-tetra-O-benzoyl-1-thio-β-D-galactopyranoside (formula 14:

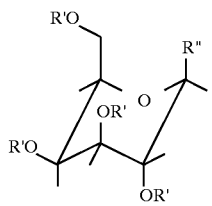

wherein R'=benzoyl and R"=—SC$_2$H$_5$) is prepared in a manner known per se from 1,2,3,4,6-penta-O-acetyl-β-D-galactopyranoside by successively reacting with a ethanethiol in the presence of tin(IV)chloride, potassium tert.butylate and finally benzoyl chloride.

f) 2-Hydroxyethyl 2,3,4,6-tetra-O-benzoyl-β-D-galactopyranoside (compound 14b having the formula 14:

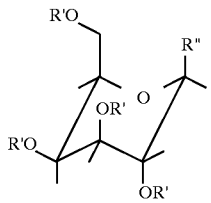

wherein R'=Bzl and R"=—O(CH$_2$)$_2$OH), 3-hydroxypropyl 2,3,4,6-tetra-O-benzoyl-β-D-galactopyranoside (compound 14c having the formula 14:

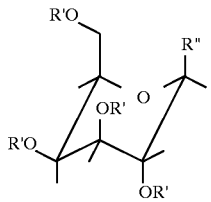

wherein R'=Bzl and R"=—O(CH$_2$)$_3$OH), 5-hydroxy-3-oxapentane 2,3,4,6-tetra-O-benzoyl-β-D-galactopyranoside (compound 14d having the formula 14:

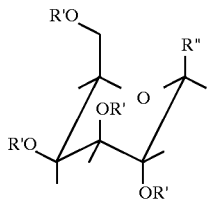

wherein R'=Bzl and R"=—O[C(CH$_2$)$_2$O]$_2$H) and 11-hydroxy-3,6,9-trioxaundecane 2,3,4,6-tetra-O-benzoyl-β-D-galactopyranoside (compound 14e having the formula 14:

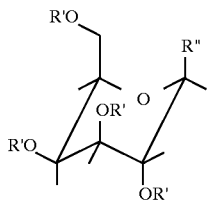

wherein R'=Bzl and R"=—O[(CH$_2$)$_2$O]$_4$H) are prepared in a manner known per se by a reaction of the compound obtained under (e) with ethylene glycol, propanediol, diethylene glycol or tetraethylene glycol in the presence of N-iodosuccinimide and trifluoromethanesulfonic acid.

g) N-[tris-O-(oligo-oxaalkyl-β-D-galactopyranosyl)methoxymethyl]methyl-$N^\alpha$-(1-(6-methyl)adipyl) glycinamide (formula 15b through 15e):

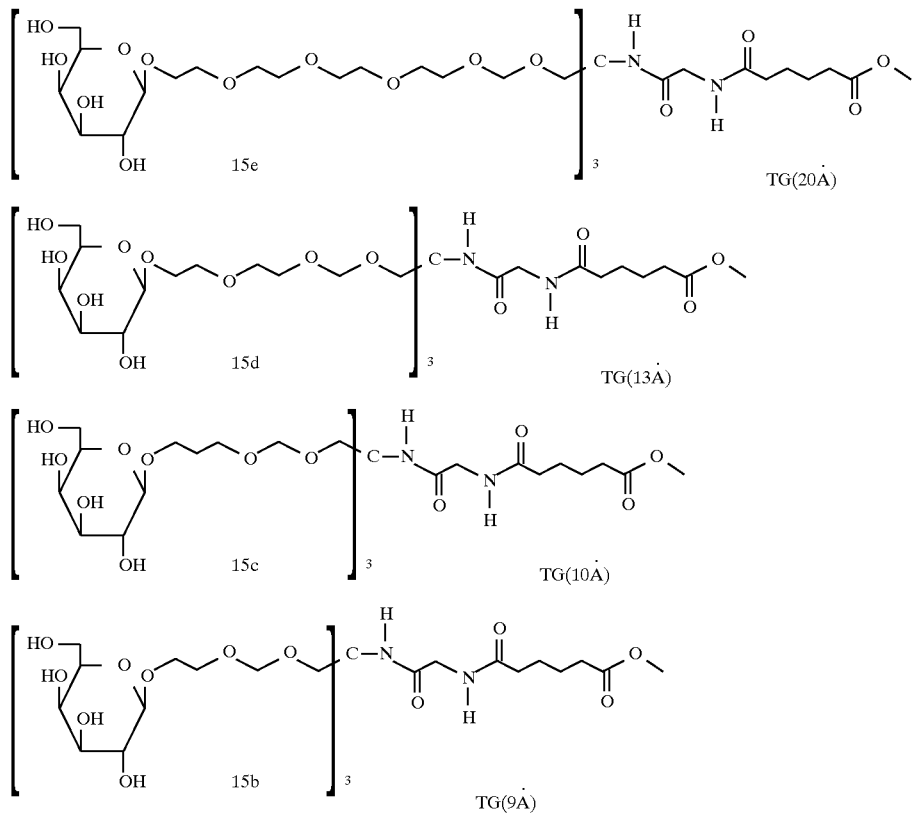

is prepared in a manner known per se by bringing together one of the compounds 14b through 14e with the compound obtained under (d) in the presence of trifluoromethanesulfonic acid and N-iodosuccinimide and subsequently treating the product with potassium tert.butylate.

A second example of a method according to the invention for the preparation of cluster glycosides having an elongated flexible and hydrophilic chain between the glycoside and the branching point of the cluster is a method comprising the following steps:

a) 1-Nitro 4-hydroxy-1,1-bis(hydroxypropyl)butane (formula 16:

[(RO(CH$_2$)$_3$—]$_3$C—R'        (16)

wherein R=H and R'=NO$_2$) is reduced in a manner known per se by means of Zn/HCl or LiAlH$_4$ to 1-amino 4-hydroxy-1,1-bis(hydroxypropyl)butane (formula 16: [(RO (CH$_2$)$_3$—]$_3$ C—R', wherein R=H and R'=NH$_2$). The amino group of this compound is then protected in a manner known per se with a trifluoroacetyl group by a reaction with trifluoroacetic acid anhydride in the presence of an equivalent amount of diisopropylethanolamine to form 1-N-(4-hydroxy-1,1-bis(hydroxypropyl)butyl)trifluoroacetamide (formula 16: [(RO(CH$_2$)$_3$—]$_3$C—R', wherein R=H and R'=—NHCOCF$_3$).

b) N-[tris[[(methylthiomethyl)oxy]propyl]methyl]-2,2,2-trifluoroacetamide (formula 16: [(RO(CH$_2$)$_3$—]$_3$C—R', wherein R=—CH$_2$SCH$_3$ and R'=—NHCOCF$_3$) is prepared in a manner known per se by reacting the compound obtained under (a) with dimethyl sulfide in the presence of benzoyl peroxide.

c) Derivatization of the compound obtained under (b) with the alkanol 11-hydroxy-3,6,9-trioxaundecane 2,3, 4,6-tetra-O-benzoyl-β-D-galactopyranoside (compound 14e) occurs in a manner known per se by reaction in the presence of N-iodosuccinimide and trifluoromethanesulfonic acid. A debenzoylation of the formed product by means of a treatment with potassium tert.butylate yields a compound of formula 17, wherein R=H and Q$^1$=—COCF$_3$.

d) After removal of the protecting trifluoroacetyl group by treatment of the compound obtained under (c) with piperidine in aqueous solution, the de-protected amino group can be derivatized with an end group Z via an oligopeptide-like spacer X$^3$ of a length of 10–15 Å.

A third example of a method according to the invention for the preparation of cluster glycosides having an elongated flexible and hydrophilic spacer between the glycoside and the branching point of the cluster involves the following steps.

a) 1-O-methyl-2,3,4-triallyl-β-D-glucopyranosyl-6-phenacetyl ester is prepared from 1-O-methyl β-D-glucose acid by reaction with phenacetylchloride and subsequent reaction of the 2,3,4-hydroxy groups with allylbromide in pyridine.

b) 1-O-methyl-2,3,4-tris(propyl 2-aminoethyl sulfide)-β-D-glucopyranoses-6-phenacetyl ester was prepared from 1-O-methyl-2,3,4-triallyl-β-D-glucopyranose-6-phenacetyl ester by photoactivation of the compound in the presence of 3-amino 1-propanethiol.

c) 1-O-methyl 2,3,4-tris(propyl 2-(N-ethylthioureido-N'-[p-(β-D-galactopyranosyl)phenylene)]-sulfide)-β-D-glucopyranose 6-phenacetyl ester is synthesized from by reacting 1-O-methyl 2,3,4-tris(propyl 2-aminoethyl sulfide) β-D-glucopyranose 6-phenacetyl ester with 1,5 equivalents of 1-phenyl-(β-D-galactopyranosyl) 4-isothiocyanate.

d) 1-O-methyl 2,3,4-tris(propyl 2-(N-ethylthioureido-N'-[p-β-D-galactopyranosyl)phenylene)]sulfide)-β-D-glucopyranose (formula 23):

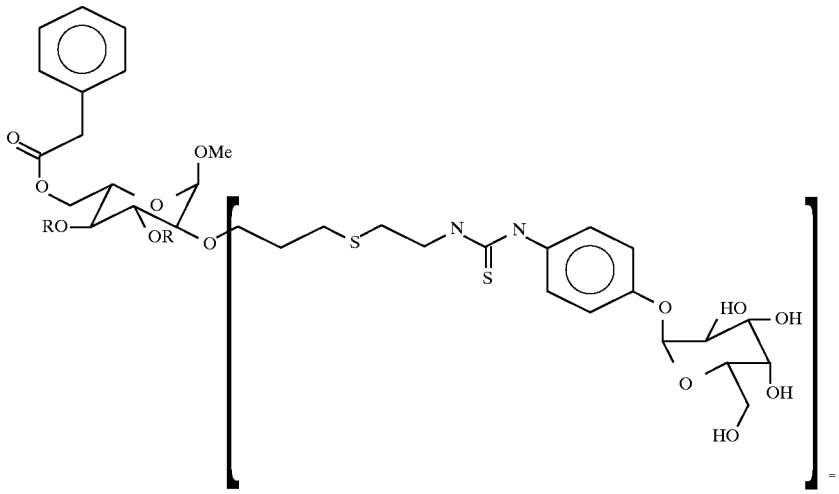

23 is prepared from 1-O-methyl 2,3,4-tris(propyl 2-(N-ethylthioureido-N'-[p-(β-D-galactopyranosyl) phenylene)]sulfide)-β-D-glucopyranose 6-phenacetyl ester by enzymatic digestion at 37° C. using phenylacetyl esterase.

The invention will be further explained in and by the following examples.

EXAMPLE 1

The compounds were prepared through the following steps (the starting materials mentioned are commercial products of p.a. quality):

a) 1-Methyl-6-succinimidyl adipate (formula 12):

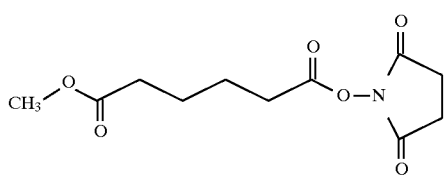

12

To a solution of 1.6 g (100 mmol) 1-methyl adipate in 100 ml acetone, 11.6 g (100 mmol) N-hydroxysuccinimide was added. Then the coupling was initiated by adding 22.8 g (110 mmol) N,N'-dicyclohexylcarbodiimide in 100 ml acetone.

After stirring at 20° C. for 2 h, the precipitate was removed via filtration. The filtrate was evaporated to dryness and chromatographed over 150 ml kieselgel column with 5% methanol in dichloromethane as eluent. Fractions containing the product contemplated were put together and the solvent was removed. Yield: 24.3 g pure 1-methyl-6-succinimidyl adipate (94 mmol; 94%).

b) N-(hydroxy-1,1-bis(hydroxymethyl)ethyl)-N$^\alpha$-(benzyloxy-carbonyl) glycinamide (formula 13: (ROCH$_2$-)$_3$C-NHCOCH$_2$NHQ$^1$, wherein R=H and Q$^1$=BOC).

To a solution of 1.8 g (tris-O-hydroxymethyl) aminomethane (15 mmol) and 3.15 g (15 mmol) N-benzyloxycarbonyl glycine in 50 ml dimethyl formamide, 3.7 g (17 mmol) N,N'-dicyclohexylcarbodiimide was added and the suspension was stirred at 20° C. for 2 days. After the reaction the suspension was filtered and the solvent was removed by evaporation. After purification of the residue over a kieselgel column (150 g) with 10% methanol in dichloromethane as eluent, 2.25 g (7.1 mmol, 47%) white crystals of the title compound were harvested.

c) N-(2-hydroxy-1,1-bis(hydroxymethyl)ethyl)-N$^\alpha$-(1-(6-methyl)adipyl)glycinamide (compound of formula 13: (ROCH$_2$-)$_3$C-NHCOCH$_2$NHQ$^1$, wherein R=H and Q$^1$=-CO(CH$_2$)$_4$COOCH$_3$).

The protecting N-benzyloxycarbonyl group of the compound obtained under (b) was removed by means of reductive hydrogenolysis. To that end, 15.6 g (50 mmol) of the compound obtained under (b) was dissolved in 200 ml of an ethanol/methanol mixture (1/1, v/v) and the solution was dispersed with N$_2$. Then, 200 mg Pd/C was added and the solution was saturated with H$_2$ at 20° C. and atmospheric pressure for 2 hours. After reduction the palladium/carbon was filtered off and the solvent was evaporated.

The coarse reaction product (formula 13: (ROCH$_2$-)$_3$C—NHCOCH$_2$NHQ$^1$, wherein R=Q$^1$=H) was used directly for derivatization with formula 12:

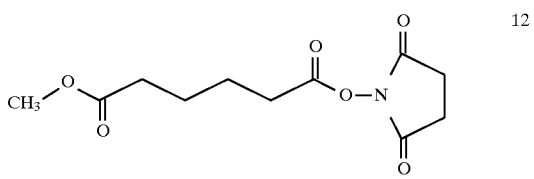

12

Of these compounds of formulae 12 and 13, 12.4 g (50 mmol) was dissolved in 100 ml dimethyl formamide and incubated at 20° C. for 3 hours, whereafter the suspension was stored at 4° C. for 18 h. The precipitate was removed by means of filtration and the filtrate was evaporated. The residue was purified over a kieselgel column (200 g) with 20% methanol in dichloromethane. The product eluted off the column directly after the N-hydroxy-succinimidyl peak. After removal of the solvent, 12.8 g white, amorphous powder (40 mmol), 80%) remained.

d) Thiomethylation of the triol to N-[tris[[(methylthio-methyl)oxy]methyl]methyl]-N$^\alpha$-(1-(6-methyl)adipyl) glycinamide (formula 13: (ROCH$_2$—)$_3$C—NHCOCH$_2$NHQ$^1$, wherein R=—CH$_2$SCH$_3$ and $^1$=—CO(CH$_2$)$_4$COOCH3).

Thiomethylation was performed according to the method of Medina et al. (ref. 16). To 0.96 g (3 mmol) of the compound obtained under (c), dissolved in 20 ml ice-cold acetonitrile, 4.6 ml (54 mmol) dimethyl sulfide and 6.5 g (27 mmol) benzoyl peroxide were added. After incubation at 0° C. for 3 hours, 20 ml ethyl acetate was added and the solution was extracted twice with 25 ml 0.1N NaOH. The organic phases were collected, dried with MgSO₄ and evaporated. The product was subsequently separated by chromatography over a LH20 column (70×2.5 cm) and chromatography over a kieselgel column (200 g) with dichloromethane as eluent. Crystallization from ether/ petroleum ether (60°–40°) yielded 1.03 g white crystals (2.0 mmol, 67%).

e) Ethyl 2,3,4,6-tetra-O-benzoyl-1-thio-β-D-galactopyranoside (formula 14:

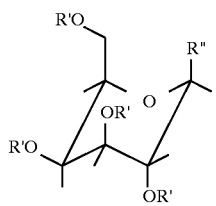

wherein R'=Bzl and R"=-SC₂H₅).

Of β-D-galactopyranosyl pentaacetate, 7.8 g was dissolved in 50 ml dichloroethane. The solvent was removed, the residue was included in 75 ml dichloroethane and 1.63 ml (22 mmol) ethanethiol was added. The solution was placed on ice and 0.35 ml (3 mmol) tin(IV)chloride was added in drops. The solution was incubated for 1 hour. After complete reaction the incubate was extracted with, successively, twice 50 ml 1M potassium fluoride and 10% (v/v) NaHCO₃ in water. The organic phase was dried with the aid of MgSO₄ and subsequently evaporated. Then residue was dissolved in 100 ml methanol with 0.5 g potassium butylate added thereto. The suspension was stirred at 20° C. for 1 hour and neutralized by addition of Dowex/pyridine. After filtration of the Dowex the solvent was evaporated. The residue was included in 50 ml pyridine and acylation was initiated via addition of 12.5 ml (120 mmol) benzoyl chloride. After reaction at 20° C. for 1 hour the excessive benzoyl chloride was inactivated by addition of H₂O whereafter the solvent was evaporated. The oily residue, after being dissolved in 50 ml dichloromethane, was washed with 50 ml H₂O and 50 ml 10% (v/v) NaHCO₃ in water. The organic phase was filtered over MgSO₄ and evaporated, which yielded 10.3 g (16 mmol; 81%) ethyl-2,3,4,6-tetra-O-benzoyl-1-thio-β-D-galactopyranoside.

f) Coupling of alkylene diols to ethyl-2,3,4,6-tetra-O-benzoyl-1-thio-β-D-galactopyranoside.

The derivatization of the compound obtained under (e) with alkylene diols (ethylene glycol, propanediol, diethylene glycol and tetraethylene glycol) to form 1-O-(2,3,4,6-tetra-O-benzoyl-β-D-galactopyranosyl)-2-ethanol (80%, compound 14b), 1-O-(2,3,4,6-tetra-O-benzoyl-β-D-galactopyranosyl)-3-propanol (83%, compound 14c), 1-O-(2,3,4,6-tetra-O-benzoyl-β-D-galactopyranosyl)-3-oxapentan-5-ol (90%, compound 14d) and 1-O-(2,3,4,6-tetra-O-benzoyl-β-D-galactopyranosyl)-3,6,9-trioxaundecan-11-ol (93%, compound 14e), was performed according to the procedure of Flügeli et al. (ref. 18).

g) Coupling of β-D-galactosyl derivatives to N-[Tris[[(methylthiomethyl)oxy]methyl]methyl]-N^α-(1-(6-methyl)adipyl)glycinamide.

100 mg (0.2 mmol) of the compound obtained under (d) and 0.72 mmol of one of the compounds obtained under (f) were dissolved in 4 ml dichloroethane/ tetrahydrofurane (1/1, v/v). Mol sieves (4 Å) were added and the suspension was stirred for 15 min while passing through N₂. The reaction was initiated by addition of 8.5 ml dichloroethane/tetrahydrofurane (1/1) having dissolved therein 170 mg (0.75 mmol) N-iodosuccinimide and 12 mg (0.075 mmol) trifluoromethanesulfonic acid. After the reaction pyridine was added, the solution was filtered off and extracted with 25 ml 1M Na₂S₂O₃ and 10% (v/v) NaHCO₃ in water. The products were isolated by means of gel exclusion over a LH20 column followed by a kieselgel column. Yield: 24–53% for the various ω-hydroxy-alkyl 2,3,4, 6-tetra-O-benzoyl-β-D-galactopyranosides.

Debenzoylation of the protected cluster glycosides occurred as follows. To 50 μmol of the relevant cluster glycoside in 10 ml methanol/1,4-dioxane (3/1), 60 mg potassium butylate was added. The solution was stirred at 20° C. for 4 hours. After the reaction the solution was neutralized by means of Dowex pyridine and the organic phase was evaporated. The residue was included in water and freeze-dried. After a gel exclusion over a S100 column the pure product of formulae 15b–15e was isolated.

EXAMPLE 2

It is possible to calculate the optimum molecule structure of the compounds thus prepared by means of minimal-mechanical energy calculations. This enables us to calculate the spatial distance of the neighbouring sugar groups within the cluster glycosides in question. The results of such a calculation for the cluster glycosides prepared are specified in the following Table:

Table 1: Effect of the spacer $X^1$ on the distance of neighbouring sugar groups within a cluster glycoside.

| Compound | | Length | Distance** |
|---|---|---|---|
| 15a | TG (4Å) | 3.7 Å | 5.9 Å |
| 15b | TG (9Å) | 9.2 Å | 14.2 Å |
| 15c | TG (10Å) | 10.4 Å | 16.5 Å |
| 15d | TG (13Å) | 12.6 Å | 19.4 Å |
| 15e | TG (20Å) | 19.5 Å | 31.5 Å |

*) Maximum chain length, defined as the distance between the anomeric center of the sugar and the branching point of the cluster glycoside.

**) Distance between two neighbouring sugar groups within a cluster sugar molecule.

It is clear from Table I that the maximum realizable distance between two neighbouring sugar groups within a cluster increases with an increase of the length of the chain through which the sugar is immobilized to the branching point of the cluster glycoside. It also appears that, particularly with the largest chain lengths (TG(13 Å) and TG(20 Å)), the flexibility of the chain is very large, with the result that the sugar groups can occupy any theoretically permissible position in the space. As will be demonstrated in Example 3, this is of great importance for the realization of an optimum binding of the cluster glycosides to the asialoglycoprotein receptor.

EXAMPLE 3

The affinity of cluster glycosides can be verified by means of binding studies. In them, it is considered to what extent the compounds are capable of inhibiting the binding of the radioisotopically labeled asioloorosomucoid to parenchymal cells isolated from rat liver according to a previously described procedure (ref 17). The sugar concentration at which inhibition arises is a measure of the affinity.

An idea of the specificity of cluster glycosides for the asialoglycoprotein receptor on the hepatic parenchymal cell can be obtained by comparing the affinity for this receptor with the affinity for the likewise galactose recognizing Fuc/Gal receptor on the hepatic Kupffer cell. This last can be determined by means of binding studies investigating to what extent the compounds inhibit the binding of lactosylated and radioisotopically labeled low density lipoprotein ($^{125}$I-Lac-LDL) to Kupffer cells ($1$–$1.5 \times 10^6$ cells/ml). To that end, Kupffer cells in DMEM medium, supplemented with 2% BSA and 2 mM $CaCl_2$, are incubated at 4° C. for 2 h with 3 μg/ml $^{125}$I-Lac-LDL in the absence or presence of the compound, in a concentration range of 1 nM to 300 μM. After the incubation the binding of $^{125}$I-Lac-LDL to the Kupffer cells is determined in a manner identical to that for $^{125}$I-ASOR binding to liver parenchymal cells.

Table 2: Affinity of different cluster glycosides for the asialoglycoprotein receptor on the hepatic parenchymal cell. The affinity is defined as the reciprocal of the inhibition constant Ki.

|  | | Asialoglycoprotein receptor | | Fuc-Gal receptor | |
|---|---|---|---|---|---|
| Compound | (formula) | Ki (μM) | pK$_i$ (± S.E.) | Ki (μM) | pK$_i$ |
| 15a | TG (4Å) | 390 | 3.41 ± 0.08 | >>30 | <<4.5 |
| 15b | TG (9Å) | 19 | 4.72 ± 0.12 | >>100 | <<4.0 |
| 15c | TG (10Å) | 1.2 | 5.91 ± 0.09 | >>100 | <<4.0 |
| 15d | TG (13Å) | 11 | 4.95 ± 0.26 | >>100 | <<4.0 |
| 15e | TG (20Å) | 0.2 | 6.68 ± 0.14 | >>100 | <<4.0 |

It appears from FIG. 1 that an increase of the length of the glycoside spacer results in a dramatic shift of the displacement curve to the left (lower concentration). This points to an enormous increase in the potency with which the cluster glycoside is capable of displacing asialoorosomucoid from the ASGPr. In other words: the affinity expressed as the reciprocal of the inhibition constant K$_i$ increases enormously (Table 2). Thus, TG(20 Å), having a chain length of 19.5, Å has a 2,000 times higher affinity for the asialoglycoprotein receptor than TG(4 Å), (the cluster glycoside part of tris-gal-chol) having a chain length of 3.7 Å. In addition, it can be concluded from Table 2 that the chain length is not the only parameter which determines the affinity for the ASGPr.

TG(10 Å) has a slightly higher affinity than TG(13 Å). If a more hydrophobic group is located in the direct environment of the galactose group, this apparently results in a higher affinity for the ASGPr. The studies of Connolly et al seem to confirm this (ref 20).

Figure 2:
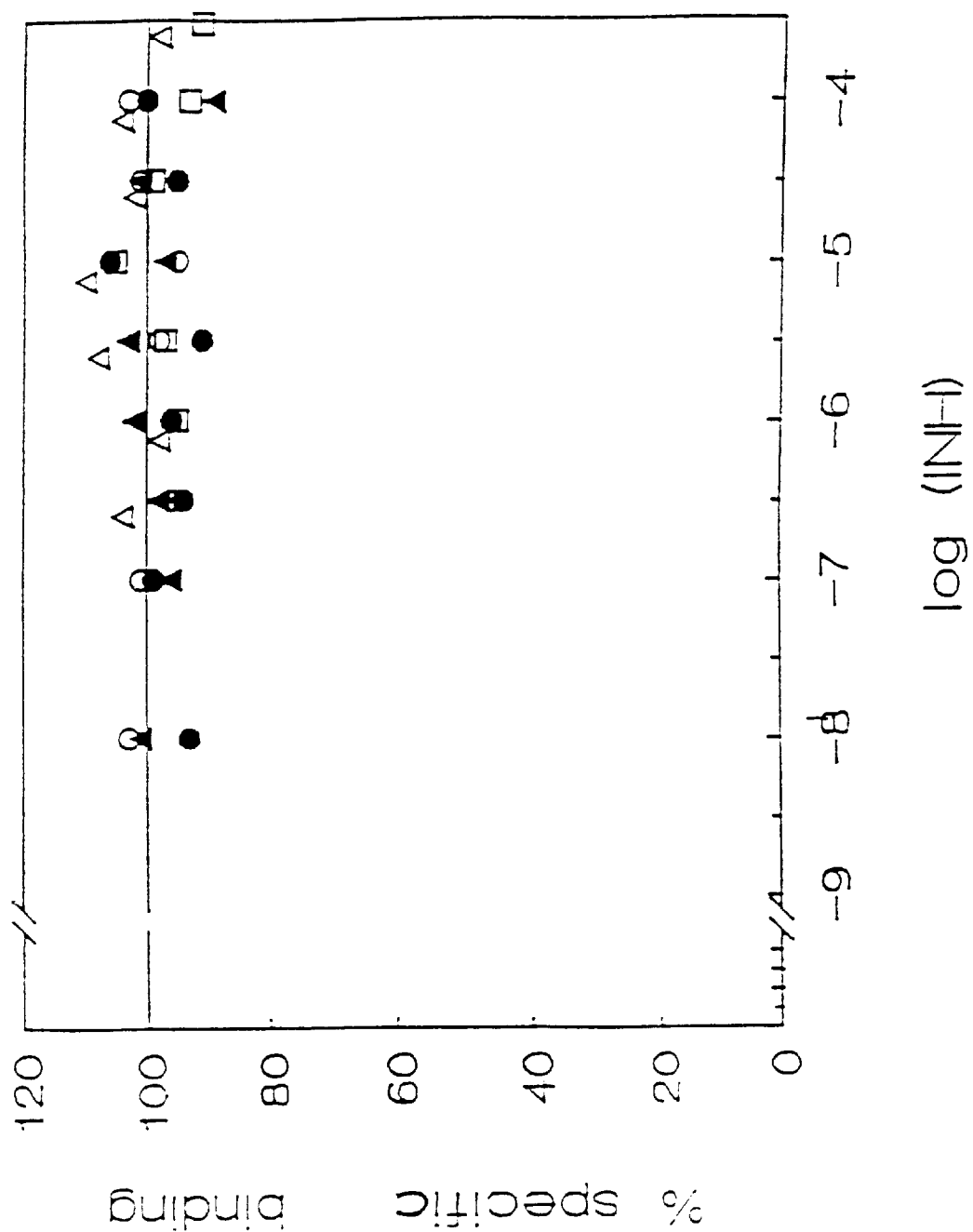
FIG. 2 illustrates the results of increasing chain length of glycoside spacers.

It appears from FIG. 2 that an increase in the chain length does not result in a significant change of the affinity for the hepatic fuc/gal receptor on the Kupffer cell. This means that, simultaneously with the affinity, also the specificity for the receptor on parenchymal cells increases with an increase in the chain length.

In contrast to Lee et al. (24), and Mary et al. (23), who have optimized the recognition of clusterglycosides by the asialoglycoprotein receptor, we have attempted to device cluster glycosides with optimal selectivity for the asialoglycoprotein receptor. This implies that cluster glycosides comprising a high density of galactose units, located at a small distance from each other, as in oligomeric tris(gal) compounds (having hydrophobic spacer molecules) or in other high valency clusters, should be avoided. These compounds will display a higher affinity for the fucose/galactose receptor on the Kupffer cell, and thus a lower specificity towards the asialoglycoprotein receptor (ref.22).

Particularly when aiming at an application of the cluster glycoside in the targeting of (lipo)protein or liposome derived drug carriers to the parenchymal liver cell this is of importance.

The cluster glycoside with the longest spacer, TG(20 Å), is, in view of its high affinity and specificity for the asialoglycoprotein receptors on the parenchymal cells of the liver, a promising ligand for functionalization into a hypolipidemic therapeutic or a hepatic drug carrier.

EXAMPLE 4

The preparation of a possible glycolipid starting from the cluster glycoside TG(20 Å):

a) N-[tris-O-(3,6,9-trioxaundecanyl-β-D-galactopyranosyl)-methoxymethyl]methyl-N$^\alpha$-1-(adipyl)glycinamide (formula 18):

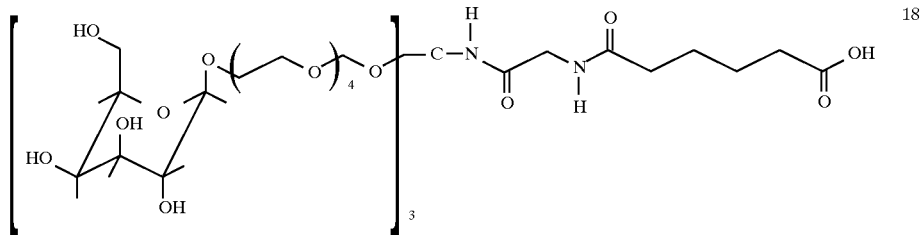

500 mg (0.35 mmol) TG(20 Å), the compound 15e having the formula 15e:

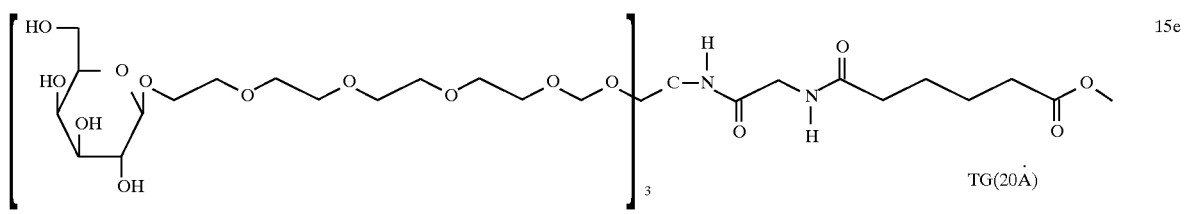

was dissolved in 9.75 ml of a 1,4-dioxane: $H_2O$ mixture (77:23) and 0.25 ml 4N sodium hydroxide was added. The solution was stirred at room temperature for 15 minutes, whereafter the base was neutralized with acetic acid. Then the solvent was evaporated and the residue chromatographed over a Sephacryl S100-HiLoad column. Yield: 340 mg (72%).

b) Glycine-(5-cholesten-3β-ylester)-hydrotrifluoroacetate (formula 19):

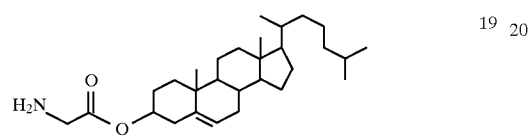

3.87 g (10 mmol) cholesterol was added to a solution of 890 mg (5 mmol) N-benzyloxycarbonyl glycine and 1.03 g (5 mmol) N,N-dicyclohexylcarbodiimide in 100 ml dichloroethane. The reaction was started by addition of a catalytic amount of 120 mg (1 mmol) N,N-dimethylaminopyridine. After 3 hours incubation at 50° C. the precipitate was filtered off and the filtrate was extracted with, successively, 2 times 100 ml 10% $NaHCO_3$ and water. The organic phase was dried above sodium sulfate and the solvent was removed. Then the residue was chromatographed over a kieselgel 60 column with 20% methanol in dichloromethane as eluent. The product was finally crystallized from ether/water. Yield: 2.23 g (82%) N-benzyloxycarbonyl-glycine-(5-cholesten-3β-ylester). The benzyloxycarbonyl group of this compound (0.55 g; 1 mmol) was removed by a treatment with 10 ml 20% trifluoroacetic acid in dichloromethane at 20° C. for 30 min. After de-protection, toluene was added and the solvent was evaporated. The pure product was crystallized from an ethanol/dichloromethane mixture as the trifluoroacetate salt. Yield: 520 mg (92%) of the compound of formula 19:

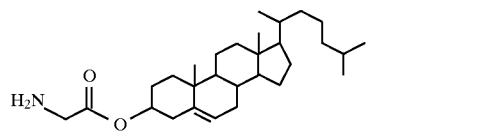

c) Preparation of N,N-[tris-O-(3,6,9-trioxaundecanyl-β-D-galactopyranosyl)methoxymethyl]methyl-$N^\alpha$-(1-(6-(5-cholesten-3β-yloxy)glycyl)adipyl)glycinamide (formula 20):

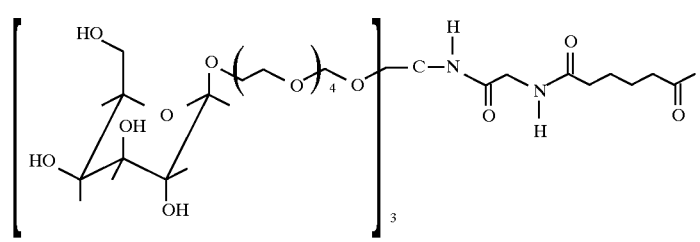

340 mg (0.24 mmol) of the compound of formula 18, 80 μl (0.5 mmol) diisopropylethylamine (0.5 mmol, 80 μl) and 230 mg (0.5 mmol) of the compound of formula 19 were dissolved in 7 ml dimethylacetamide. The coupling was initiated with addition of 100 mg (0.25 mmol) BOP reagent. After incubation at 20° C. for 30 min, the solvent was evaporated, the residue was included in water and the solution was freeze-dried. The coarse product was purified by means of chromatography over a LH20 column with methanol as eluent, followed by a kieselgel 60 column with methanol as eluent. Yield: 201 mg of the compound of formula 20 (46%; TG(20 Å)-chol)

EXAMPLE 5

The thus prepared compound TG(20 Å)-chol (formula 20):

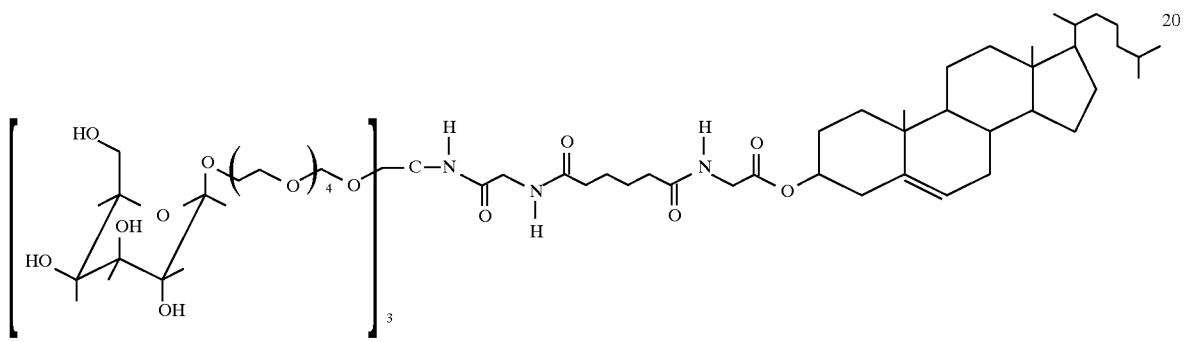

can be used to lower the serum cholesterol level.

This was verified as follows. Male rats (250–300 g) were anesthetized by means of ether, whereafter 500 gl PBS, having dissolved therein 0.56 mg, 0.18 mg, 0.056 mg or 0 mg TG(20 Å)-chol (formula 20) or 0.56 mg tris-glu-chol (formula 21):

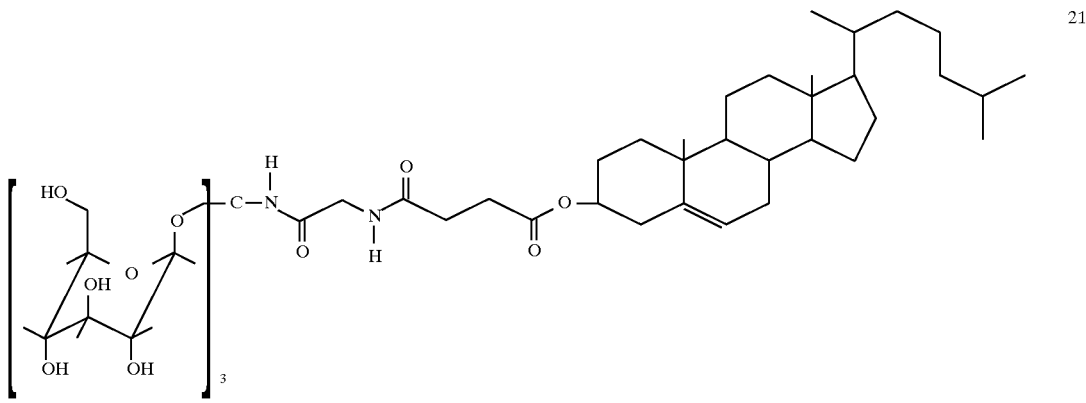

was injected into the vena penis. At the times indicated in FIG. 3, blood samples of 300 μl were taken by means of orbital puncture. The blood samples were centrifuged (5 min; 1500 g) and the serum was used for a cholesterol assay by means of the CHOD-PAP kit of Boehringer Mannheim. 24 Hours after injection the rat was bled. The blood was centrifuged whereafter the serum was pipeted. Then the serum was subjected to gradient density ultracentrifugation and the various lipoprotein fractions were isolated: HDL (1.21<d<1.05), LDL (1.050<d<1.019), IDL (1.019<d<1.006) and VLDL (d<1.006). Finally, the total cholesterol concentrations of these lipoprotein fractions were assayed by means of the CHOD-PAP kit.

Figure 3:
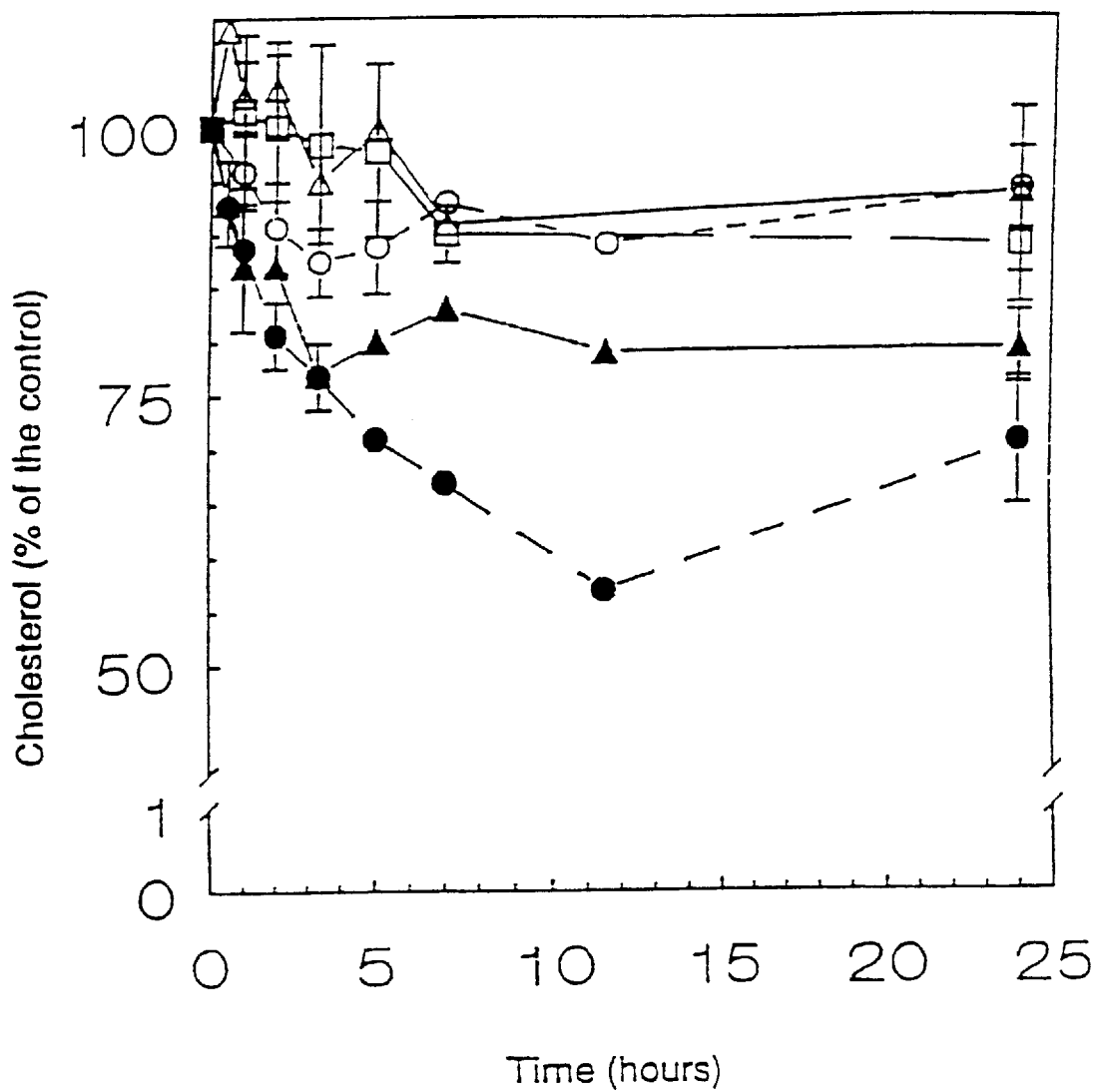
FIG. 3 illustrates the result of injecting TG(20 Å)-chol in rats.
Figure 4A:
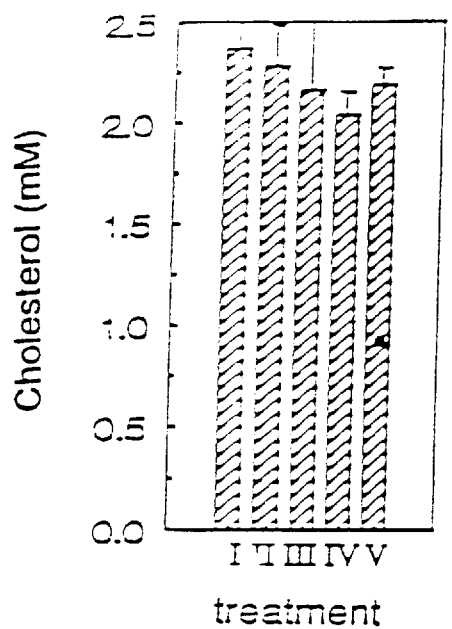
FIGS. 4A–4F illustrate the decrease of serum HDL level as a result of injecting TG(20 Å)-chol in rats.
Figure 4B:
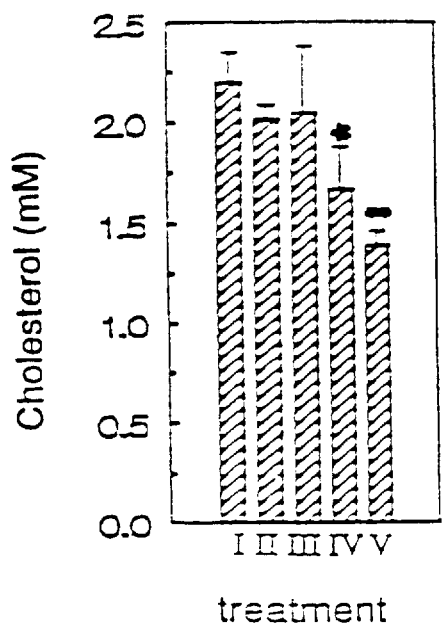
Figure 4C:
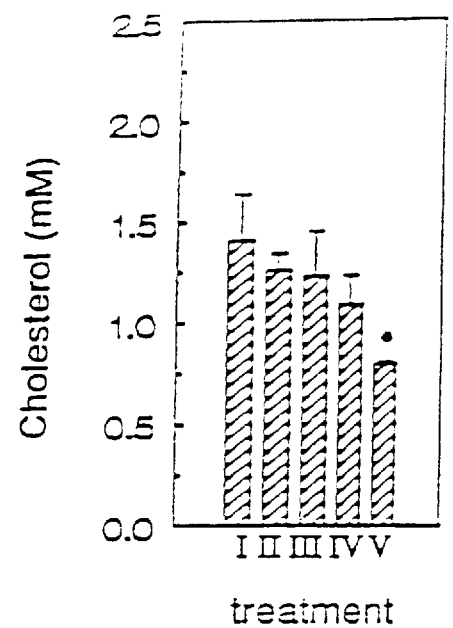
Figure 4D:
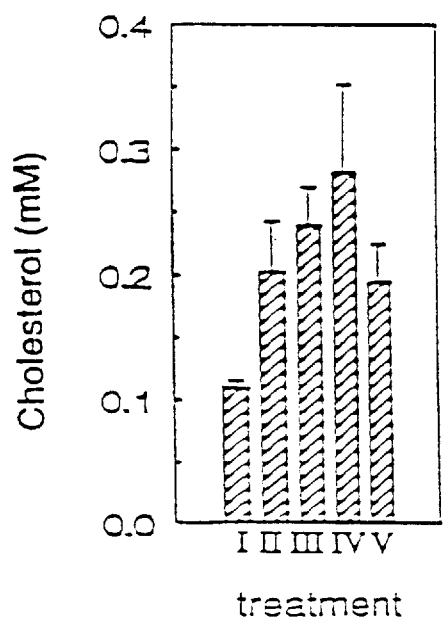
Figure 4E:
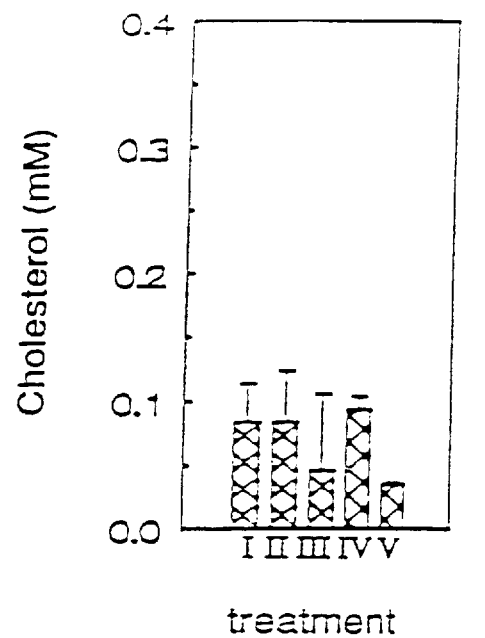
Figure 4F:
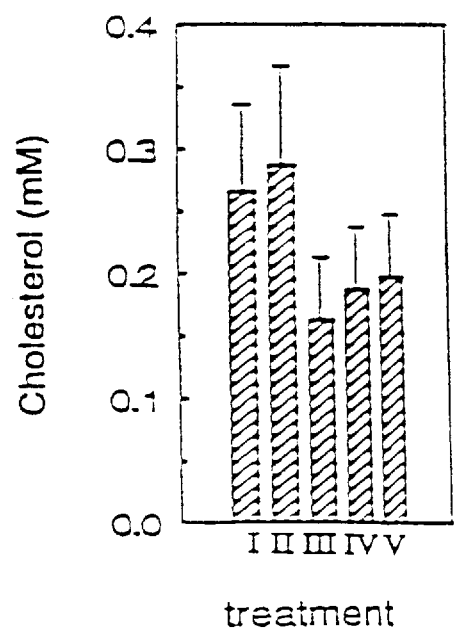

FIG. 3 shows that the total serum cholesterol level decreases as a consequence of injection of TG(20 Å)-chol. This decrease is dose-dependent. The total cholesterol content in the sera of the control rat, injected with a placebo, is constant over the time span measured. Injection of tris-glu-chol (formula 21):

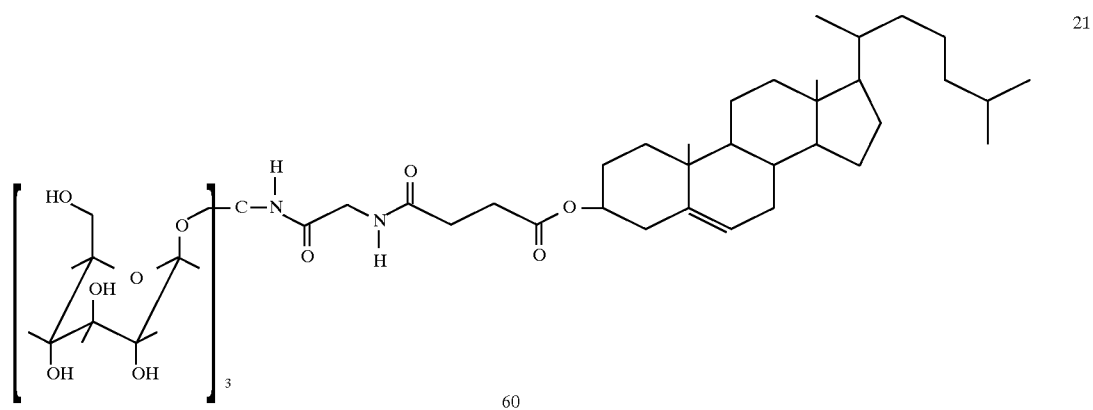

does not lead to a change in the cholesterol level either, which demonstrates the galactose-specificity of the cholesterol removal from the serum. In comparison with the previously developed tris-gal-chol (formula 22):

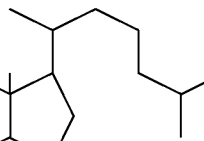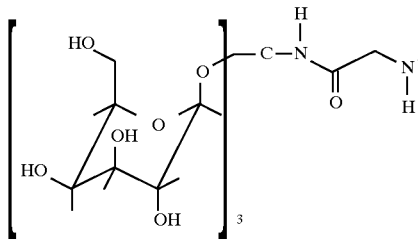

the potency has increased by at least a factor of 25 (ref 15).

Further, the persistence of the decrease in the cholesterol level is noteworthy. Even 24 hours after a single administration of 0.56 mg TG(20 Å)-chol, the cholesterol level has not returned to the control value.

The decrease of the total cholestrol level as found after 24 h is reflected in a decrease in the serum HDL level (see FIG. 4). The HDL level decreases dose-dependently and significantly after injection of TG(20 Å)-chol. The LDL level is likewise lowered at this time after administration of TG(20 Å)C. The concentrations of the other lipoproteins are not significantly affected by TG(20 Å)-chol. When intrapolating these data, however, the fact should be taken into consideration that the tested time is not optimal, that HDL is the most prominent lipoprotein in the rat (65–70%), so that accumulation of TG(20 Å)-chol will occur in HDL in particular.

Figure 5A:
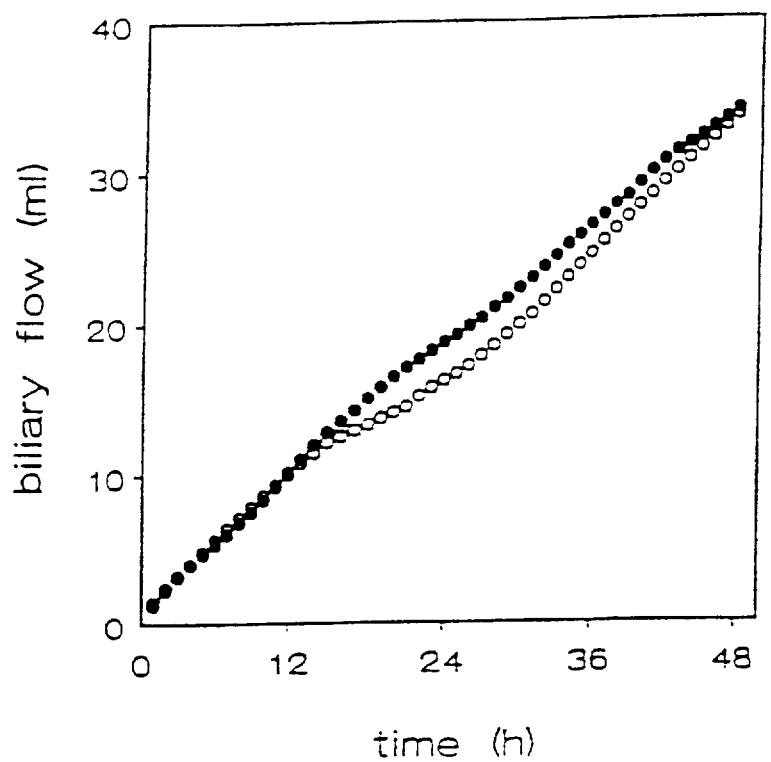
FIGS. 5A–5C illustrate the result of injection of TG(20 Å)-chol in rats.
Figure 5B:
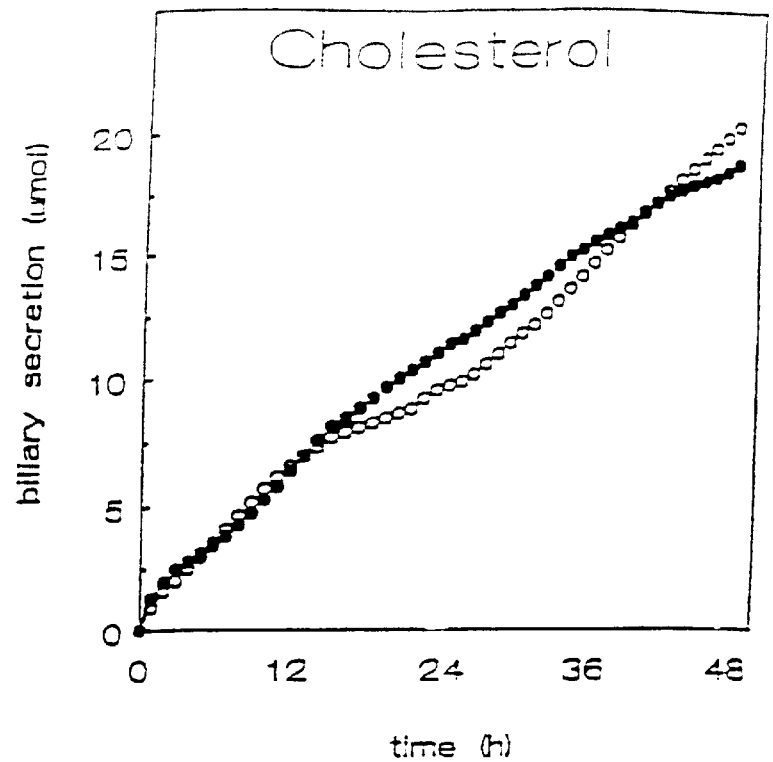
Figure 5C:
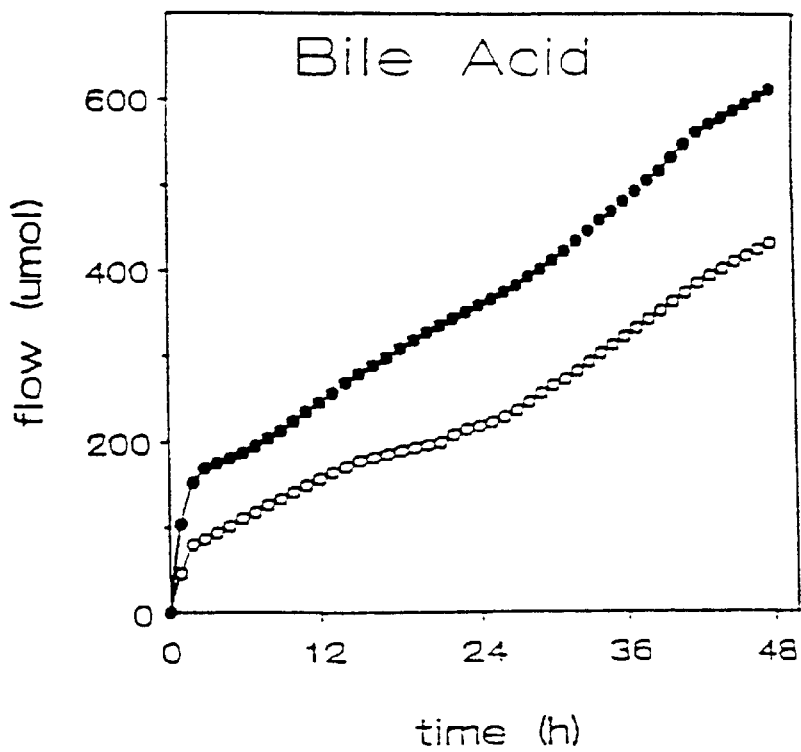

Intravenous injection of TG(20 Å)C (0.56 mg, dissolved in phosphate buffered saline) in rats, provided with catheters in duodenum, bile-duct and heart vene, also enhances the biliary secretion of bile acids from the liver leaving the biliary flow and the biliary secretion of cholesterol unaltered. Apparently, the TG(20 Å)C-induced increase in the uptake of lipoprotein-derived cholesterol is efficiently coupled to bile-acid secretion in rats. This might have important implications for potential application of TG(20 Å)C as a hypocholesterolemic therapeutic. (See FIG. 5.)

EXAMPLE 6

Figure 6A:
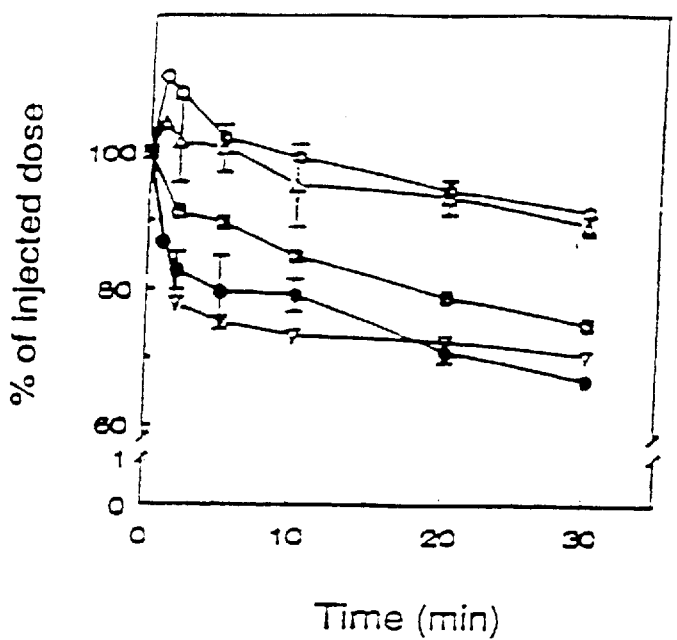
FIGS. 6A–6B illustrate the changed behavior of LDL in rats after intravenous injection of TG(20 Å)-chol.
Figure 6B:
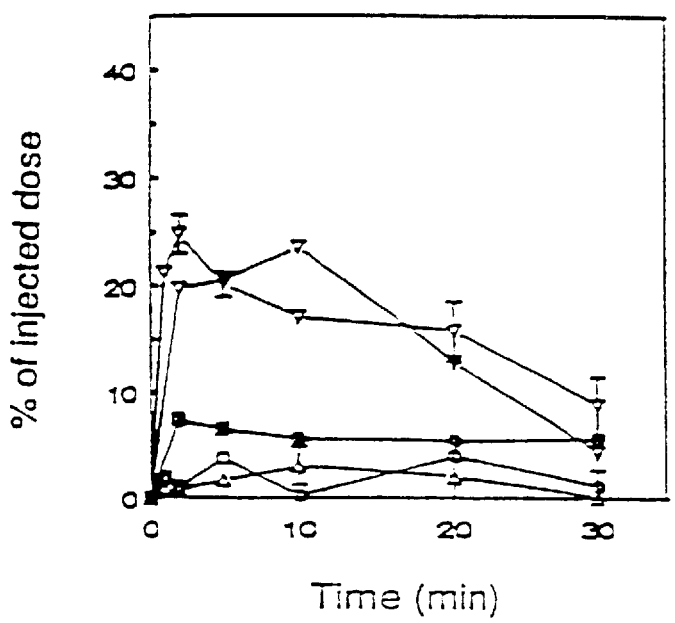
Figure 7:
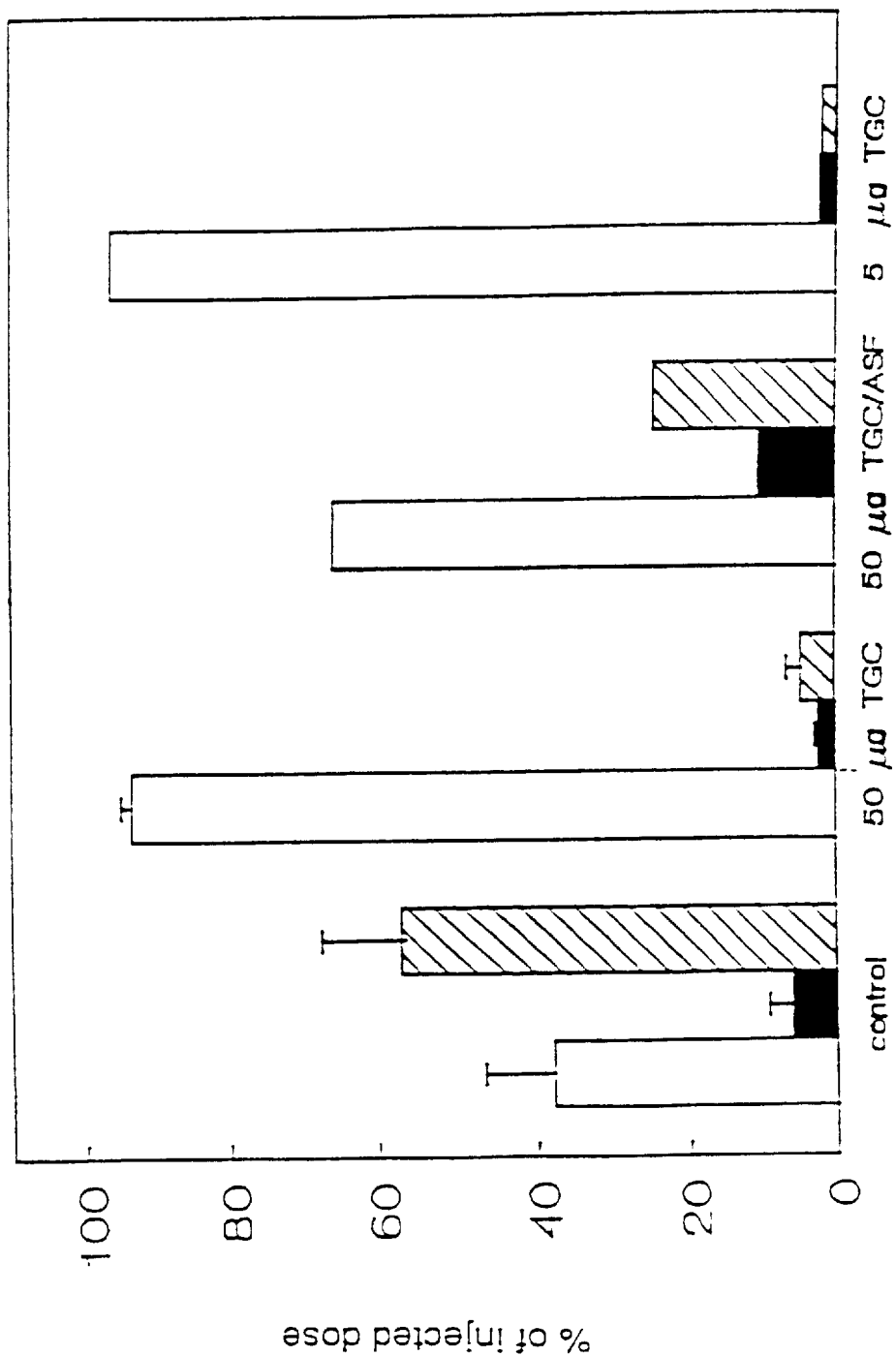
FIG. 7 illustrates the results of LDL uptake by the liver in rats.

The so prepared compound TG(20 Å)-chol (formula 20):

charged with TG(20 Å)-chol according to a procedure that is known per se and the in vivo behaviour of the particle was studied. LDL (50 μg) in PBS was incubated at 20° C. for 30 min with 0, 5, 15 and 50 μg TG(20Å(-chol). This charge led to a changed behaviour of the LDL after intravenous injection into rats. This is illustrated in FIG. 6. Whilst the uncharged LDL particles (labeled with $^{125}$I) disappear only slowly from the bloodstream after intravenous administration, and are taken up by the liver only to a very slight extent, the particles charged with TG(20 Å)-chol are cleared and incorporated into the liver much faster. On account of the high hydrophilicity of TG(20 Å)-chol, very rapidly an exchange of this compound occurs between LDL and other lipoproteins and lipid compartments. This then leads to a stabilization of the LDL level in the bloodstream after a few minutes. Accumulation of TG(20 Å)-chol in LDL, then, changes the physiological rate of LDL. The complex is taken up by the liver via a galactose-specific route. The liver, however, possesses two galactose-specific receptors. Now it can be verified whether the complex is taken up by the parenchymal or by the Kupffer cell on the liver. FIG. 7 shows that the LDL taken up by the liver as a result of charging with TG(20 Å)-chol is largely located in the parenchymal cell. The uncharged LDL taken up by the liver is mainly located in the Kupffer cell. Blocking the asialoglycoprotein receptor by means of preinjection of 50 mg/kg asialofetuin, 1 min before the injection of the TG(20 Å)-chol/LDL complex, results in a significant inhibition of the uptake by the liver parenchymal cell. This is an indication that charging with this compound leads to liver uptake via the asialoglycoprotein receptor in the parenchymal cell.

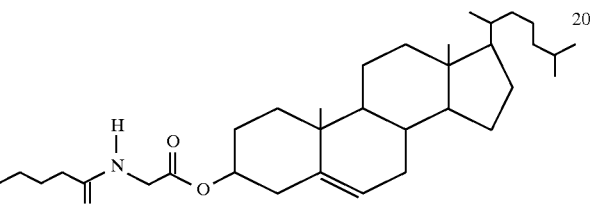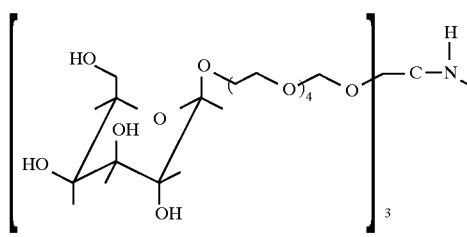

can also be used to direct LDL to the hepatic parenchymal cell. To investigate this, isolated low-density lipoprotein was This is of great importance for the possible use of TG(20 Å) (formula 15e) or TG(20 Å)-chol (formula 20):

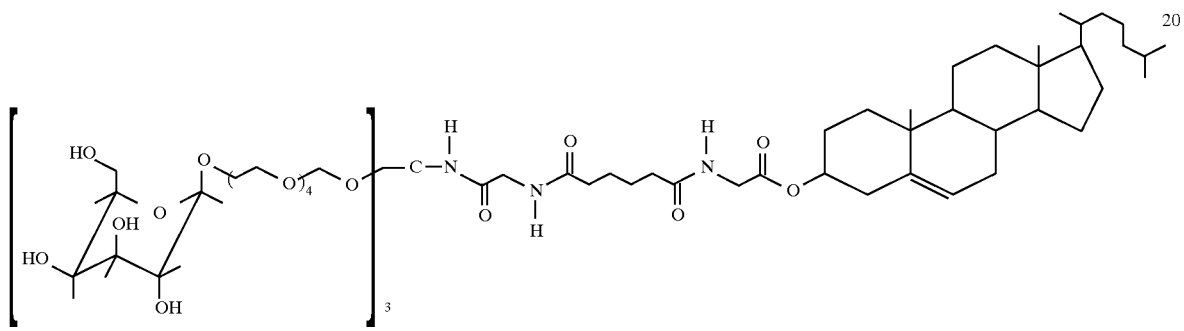

as a hypolipidemic therapeutic or as an agent to direct drug carriers to the hepatic parenchymal cell.

EXAMPLE 7

Effect of TG(20 Å)C on the in vivo fate of lipoprotein (a) (lp(a)).

Figure 8A:
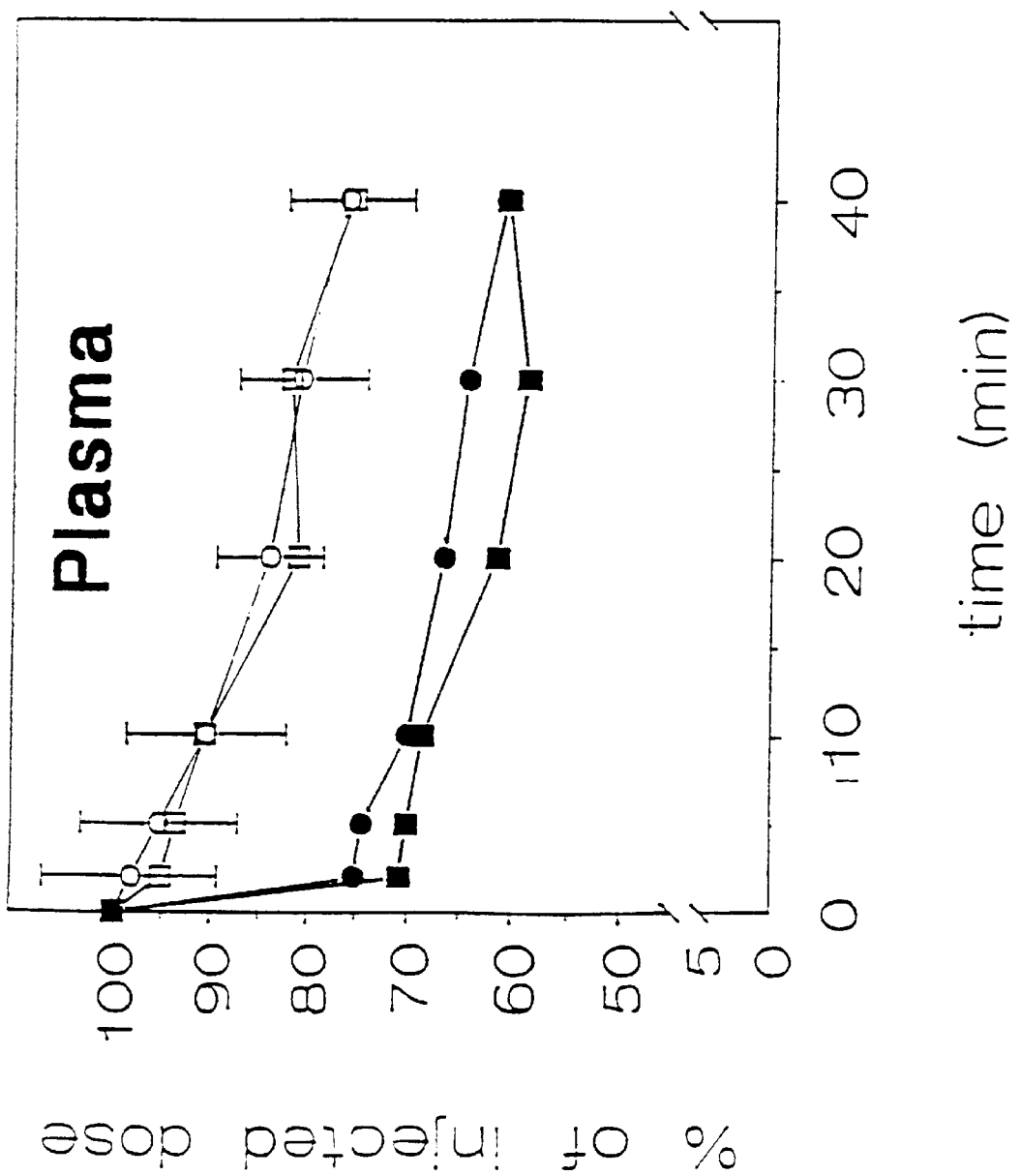
FIGS. 8A–8B illustrate the changed behavior of APO(a) in rats after intravenous injection of TG(20 Å)-chol.
Figure 8B:
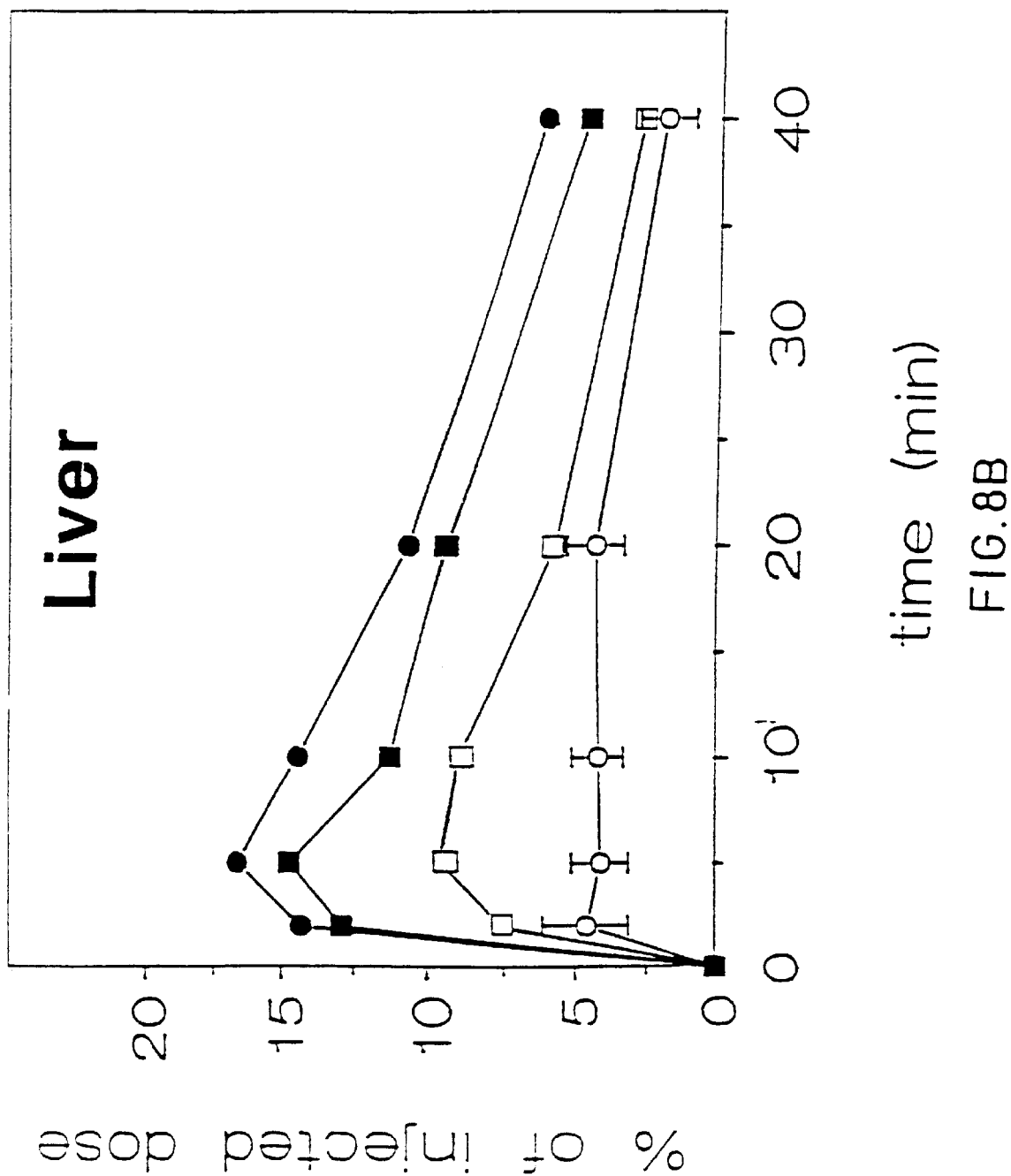
Figure 11:
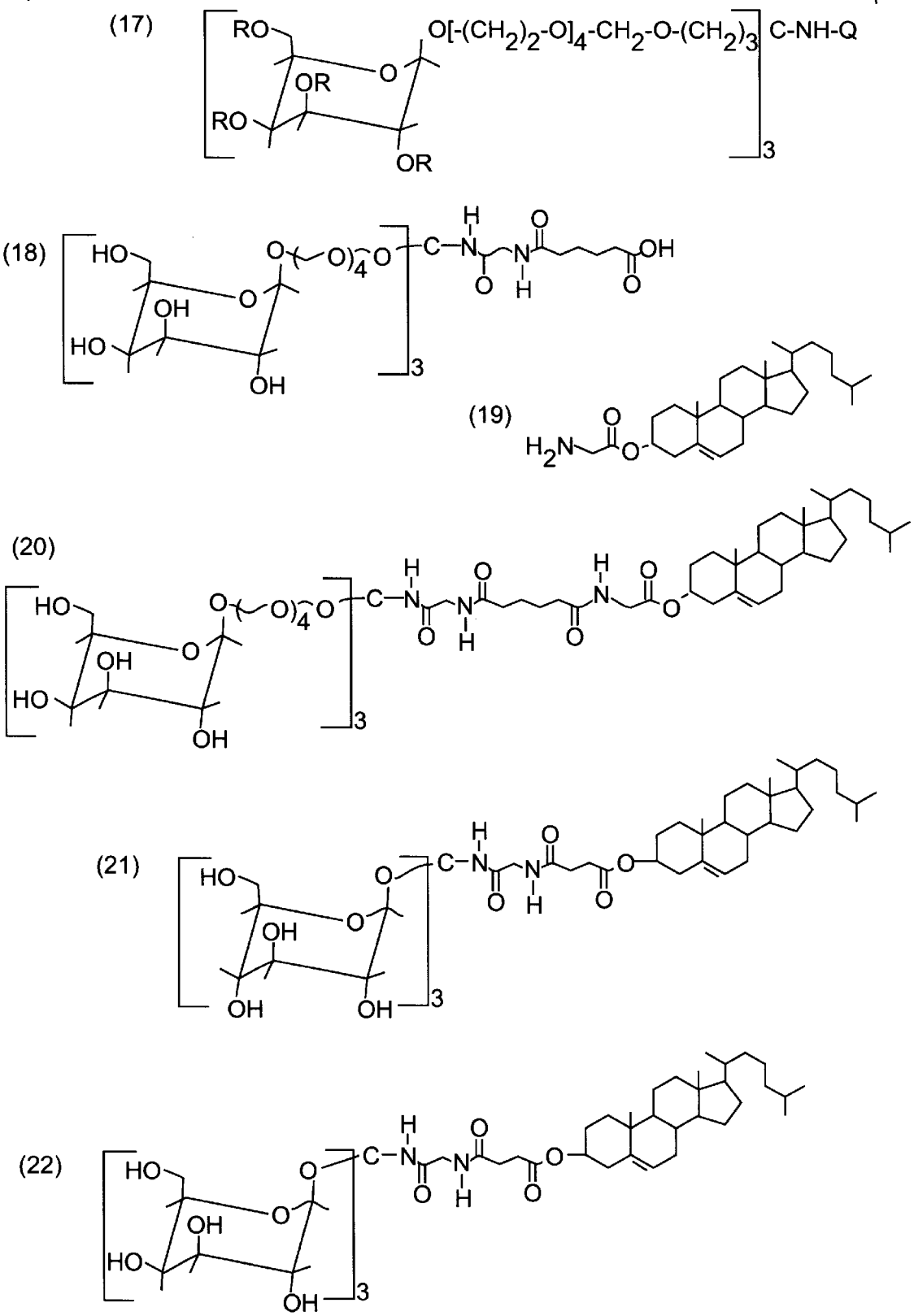
FIG. 11 depicts Formulas 17–22.
Figure 12:
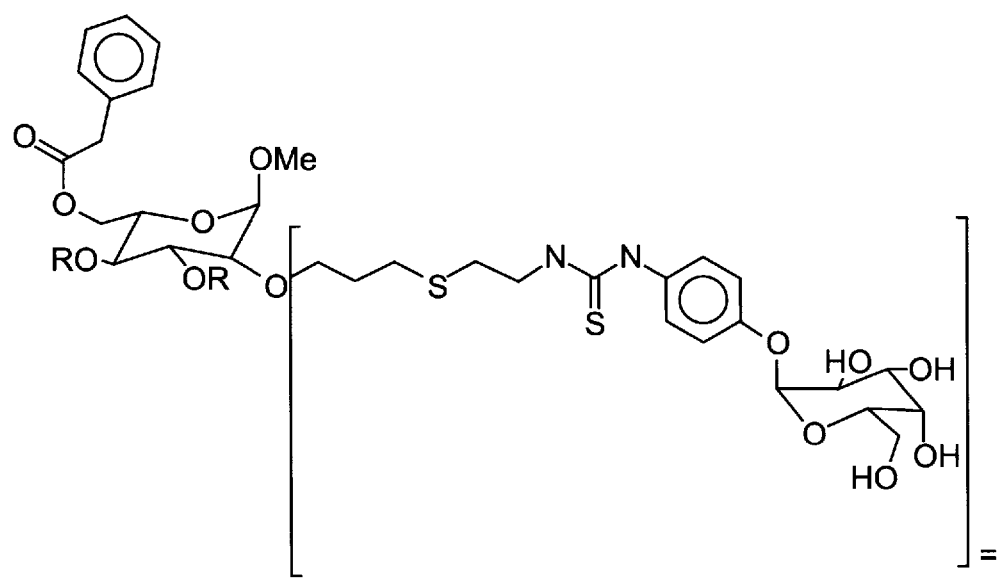
FIG. 12 depicts Formula 23.

The so prepared TG(20 Å)-chol (formula 20):

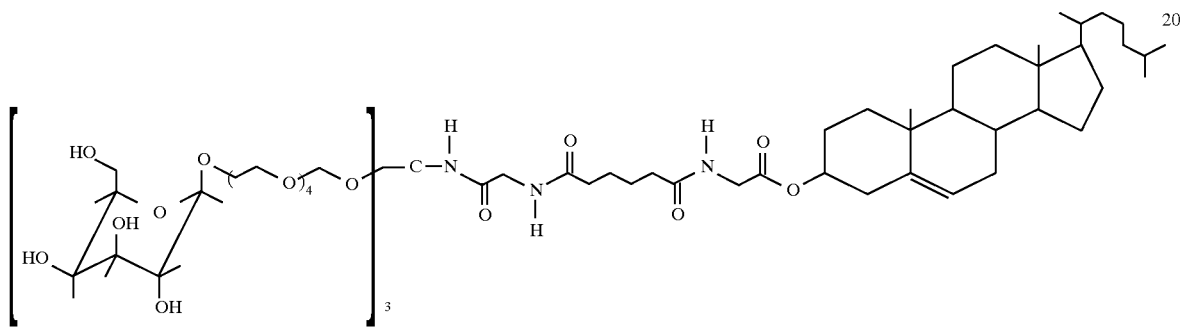

can also be used to direct apo(a) to the hepatic parenchymal cell. High levels of lp(a) are correlated with the occurence of coronary and vascular diseases. To date, an adequate clinical therapy to alleviate the pathogenesis is not available. To investigate whether TG(20 Å)C can be used to stimulate the hepatic uptake and processing of lp(a) this, isolated lp(a) was charged with TG(20 Å)-chol according to a procedure that is known per se and the in vivo behaviour of the particle was studied. Lp(a) (50 μg) in PBS was incubated at 20° C. for 30 min with 0, 5, 15 and 50 μg TG(20 Å) (-chol). This charge led to a changed behaviour of the apo(a) after intravenous injection into rats. This is illustrated in FIG. 8. Whilst the uncharged apo(a) particles (labeled with $^{125}$Å) disappear only slowly from the bloodstream after intravenous administration, and are taken up by the liver only to a very slight extent, the particles charged with TG(20 Å)-chol are cleared and incorporated into the liver much faster. On account of the high hydrophilicity of TG(20 Å)-chol, very rapidly an exchange of this compound occurs between lp(a) and other lipoproteins and lipid compartments. This then leads to a stabilization of the lp(a) level in the bloodstream after a few minutes.

Accumulation of TG(20 Å)-chol in lp(a), then, changes the physiological behaviour of lp(a). The complex is taken up by the liver via a galactose-specific route. The liver, however, possesses two galactose-specific receptors. Now it can be verified whether the complex is taken up by the parenchymal or by the Kupffer cell on the liver. Table 3 shows that the lp(a) taken up by the liver as a result of charging with TG(20 Å)-chol is largely recovered in the parenchymal cell (54+11%). The lp(a) charged with TG(4 Å)C is taken up by the liver is mainly located in the Kupffer cell, suggesting that in contrast to TG(4 Å)C, TG(20 Å)C is more efficient in targeting lp(a) to the liver parenchymal cell. Since the TG(20 Å)C induced hepatic uptake of $^{125}$I-lp(a) can be inhibited by preinjection of the rat with 150 mg of N-acetyl-galactosamine (data nor shown), this is an indication that charging with this compound leads to liver uptake via the asialoglycoprotein receptor in the parenchymal cell.

This is of great importance for the possible application of TG(20 Å), the compound 15e having the formula 15e:

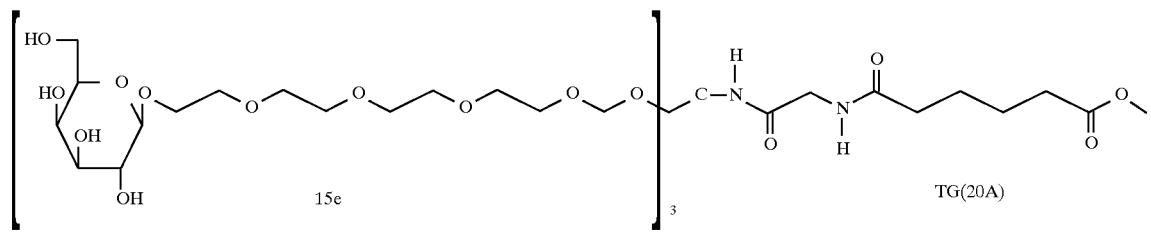

or TG(20 Å)-chol (formula 20):

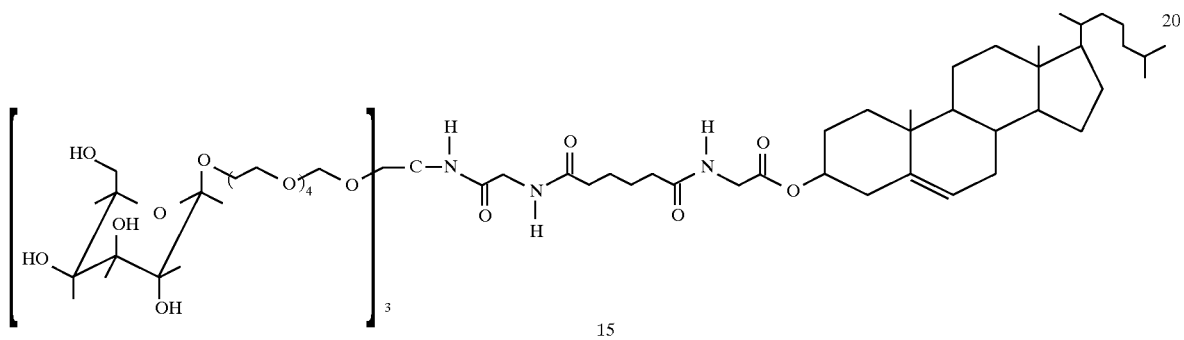

as a lp(a) lowering therapeutic.

Table 3: Contributions of various cell types to the liver association of Lp(a), loaded with various amounts of TG(20 Å)C or TG(4 Å)C.

$^{125}$I-Lp(a) (50 μg) was mixed with 50 μg of TG(20 Å)C or TG(4 Å)C in 500 μl PBS. After 30 min at room temperature, the mixtures were injected into rats at a dose of 50 μg of apolipoprotein/kg body weight. Ten minutes after injection, parenchymal, endothelial and Kupffer cells were isolated from the liver and counted for radioactivity. Values are expressed as 10–3.% of the injected dose per mg of cellular protein and are means of 3 experiments ± s.e.m.

| Cell type | Contribution to hepatic uptake (in %) | |
|---|---|---|
| | TG (4Å) C | TG (20 Å) C |
| PC | 9.4 ± 1 | 54.3 ± 11 |
| EC | 10.4 ± 3 | 8.3 ± 2 |
| KC | 80.3 ± 3 | 37.3 ± 9 |

REFERENCES

1) Chabala and Shen, Carbohydr. Res. 67: 55–63 (1978).
2) Ponpipom et al., Can. J. Chem. 58: 214–220 (1979).
3) Slama and Rando, Carbohydr. Res. 88: 213–221 (1981).
4) Roelen et al., J. Med. Chem. 34: 1036–1041 (1991).
5) Bussian and Wriston, Biochim. Biophys. Acta 471: 336–340 (1977).
6) Jonah et al., Biochim. Biophys. Acta 541: 321–333 (1978).
7) Surolia and Bacchawat, Biochim. Biophys. Acta 497: 760–765 (1977).
8) Hoekstra et al., Biochim. Biophys. Acta 603: 336–346 (1980).
9) Spanjer and Scherphof, Biochim. Biophys. Acta 734: 40–47 (1983).
10) Gosh and Bacchawat, Biochim. Biophys. Acta 632: 562–572 (1980).
11) Gosh et al., Arch. Biochem. Biophys. 206:454–457 (1981).
12) Kempen, et al., J. Med. Chem. 27: 1306–1312 (1984).
13) Van Berkel et al., J. Biol. Chem. 260: 2694–2699 (1985).
14) Van Berkel et al., J. Biol. Chem. 260: 12203–12207 (1985).
15) Kempen et al., J. Lipid Res. 28: 659–666 (1987).
16) Medina et al., Tetr. Letters 29: 3773–3776 (1988).
17) Biessen et al., in "Mechanisms of Hepatic Endocytosis", eds E. Windler & H. Greten, Z. Zuckschwerdt Verlag, Munich (Germany), pp 157–166 (1992).
18) Flügeli, P., Garegg, P. J., Löhn, H. and Norberg, T. (1987), Glycoconjugate J. 4: 97.
19) Lehrmann, M. A. and Hill, R. L. (1981), J. Biol. Chem. 261: 7419–7420.
20) Connolly, D. T., Townsend, R. P., Kawaguchi, K., Bell, W. R. and Lee, Y. C. (1982), J. Biol. Chem. 257: 939–945.
21) Goodarzi, G., Gross, S. C., Tewari, A. and Watabe, K., (1990), J. Gen. Virol. 71: 3021–3025.
22) Lehrman, M. A., Haltiwanger, R. S. and Hill R. L., J. Biol. Chem., 261: 7426–7432 (1986).
23) Mary, A., Falmagne J. B. and Trouet, A., Eur. Patent, 0,363,275
24) Lee, R. T. Lin, B., Lee, Y. C., Biochemistry, 23: 4255–4261 (1984).
25) Spiess, M., Biochemistry, 29: 10009–10018 (1990).
26) Kempen et al., U.S. Pat. No. 4,751,219.

We claim:

1. Triantennary cluster glycoside having the formula 1:

[GO—X$^1$—]$_3$A—X$^2$—Z    (2)

wherein GO is a glycoside residue selected from the group consisting of monosaccharides and disaccharides;

where X$^1$ is a long, flexible, hydrophilic spacer having about 4 atoms to about 15 atoms and having the formula:

—[HG-Alk-]$_e$— wherein HG is a hydrophilic group, wherein Alk is a branched or straight C$_1$–C$_4$ alkylene group, and wherein e is from 1–8, and wherein the Alk is arranged between two hydrophilic groups;

wherein A is a branching point of the cluster which is a carbon atom or a sugar group;

wherein X$^2$ is an end group spacer of a chain length having about 4 atoms to about 12 atoms; and wherein Z is an end group selected from the group consisting of a protected reactive group, a lipophilic group, a drug residue and a drug carrier residue, excluding a tetrakis-O-(3-carboxy-propionyl) pentaerythritol tetrakis-(1,2,3,4-tetra-O-benzyl-α-D-glucopyranosid-6-yl)tetraester, and a tetrakis-O-(3-carboxy-propionyl)pentaerythritol tetrakis-(α-D-glucopyranosid-6-yl)tetraester.

2. Triantennary cluster glycoside according to claim 1, wherein the hydrophilic spacer X$^1$ having at least two hydrophilic groups HG.

3. Triantennary cluster glycoside according to claim 1, wherein the hydrophilic group HG is selected from the group consisting of —O—, —CO—, —NH—, —CONH—, NHCO—, OCO—, and —COO—.

4. Triantennary cluster glycoside according to claim 1, wherein the hydrophilic spacer X$^1$ having the formula 2:

$$—(CHR^1)_n[O(CHR^2)_p]_rOCH_2O(CHR^3)_q— \quad (2)$$

wherein $R^1$, $R^2$ and $R^3$ are independently a hydrogen atom or a methyl group, wherein p and q are independently an integer from 1–4, and wherein n and r are independently an integer from 0–6.

5. Triantennary cluster glycoside according to claim 4, wherein $R^1$, $R^2$ and $R^3$ are independently a hydrogen atom.

6. Triantennary cluster glycoside according to claim 4, wherein n is an integer from 2–4, wherein p is an integer from 2–3, wherein q is an integer from 1–3, and wherein r is an integer from 1–5.

7. Triantennary cluster glycoside according to claim 1, wherein the glycoside residue GO is selected from the group consisting of β-D-galactosyl, 2-acetamido-2-deoxygalactopyranosyl, β-D-lactosyl, 1-phenyl-β-D-galactosyl, 1-propyl-β-D-galactosyl, and 1-butyl-β-D-galactosyl.

8. Triantennary cluster glycoside according to claim 1, wherein the chain of the end group spacer $X^2$ having at least one alkylene group and at least one hydrophilic group.

9. Triantennary cluster glycoside according to claim 8, wherein the hydrophilic group is selected from the group consisting of —O—, —CO—, —NH—, —CONH—, —NHCO—, —OCO— and COO—.

10. Triantennary cluster glycoside according to claim 9, wherein the end group spacer $X^2$ having the formula 3:

$$—NH[CO(CHR^4)_sNH]_tCO(CHR^5)_vCO[NH(CHR^6)_u CO]_w— \quad (3)$$

wherein $R^4$, $R^5$ and $R^6$ are independently a hydrogen atom or an alkyl group having 1–4 carbon atoms, wherein s, t and u are independently an integer from 1–4, and wherein v and w are independently an integer from 0–4.

11. Triantennary cluster glycoside according to claim 10, wherein $R^4$, $R^5$ and $R^6$ are independently a hydrogen atom.

12. Triantennary cluster glycoside according to claim 10, wherein v is an integer from 1–2, wherein w is an integer from 0–2, and wherein s, t and u are independently an integer from 1–4.

13. Triantennary cluster glycoside according to claim 1, wherein the end group Z is selected from the group consisting of a hydroxyl group, an alkoxy group having 1–4 carbon atoms, an amino group, a 3β-cholesterol residue, a $N_\alpha,N_\epsilon$-dioleoyl lysine residue, a 5β-cholanic acid-3α-ol oleate residue, a 5-cholenic acid-3β-ol oleate residue, a 5β-cholanic acid-3α, 12α-diol dioleate residue, and a lipoprotein residue.

14. Triantennary cluster glycoside according to claim 13, wherein the end group Z is a cholesterol residue.

15. Triantennary cluster glycoside according to claim 1, having the formula 4:

$$[GO—(CH_2CH_2O)_4CH_2O(CH_2)_q—]_3CNHCOCH_2NHCO(CH_2)_4CONHCH_2CO—Ochol \quad (4)$$

wherein q is an integer from 1–3, wherein GO is a galactose residue, and wherein —Ochol is a cholesterol residue.

16. A pharmaceutical composition comprising a triantennary cluster glycoside according to claim 1, and at least one pharmaceutically acceptable carrier.

17. Method of preparing a triantennary cluster glycoside of formula 5:

$$[GO—(CHR^1)_n[O—CHR^2)_p]_rOCH_2O(CHR^3)_q—]_3C—X^2—Z \quad (5)$$

wherein GO— is a glycoside residue selected from the group consisting of monosaccharides and disaccharides; wherein $X^2$ is an end spacer having about 4 atoms to about 12 atoms; wherein Z is an end group selected from the group consisting of an optionally protected reactive group, a lipophilic group, a drug residue and a drug carrier residue, excluding tetrakis-O-(3-carboxy-propionyl)pentaerythritol tetrakis-(1,2,3,4-tetra-O-benzyl-α-D-glucopyranosid-6-yl)tetraester or a tetrakis-O-(3-carboxy-propionyl)pentaerythritol tetrakis-(α-D-glucopyranosid-6-yl)tetraester, wherein $R^1$–$R^3$ is a hydrogen atom, and an alkyl group having 1–4 carbon atoms;

wherein p and q is an integer from 1–4; and wherein n and r is an integer from 0–6;

said method of preparing said triantennary cluster glycoside having the step of:

reacting a compound having the formula 6:

$$G'O—(CHR^1)n[O(CHR^2)_p]_rOH \quad (6)$$

wherein G'O— is a residue of a protected glycoside selected from the group consisting of monosaccharides and disaccharides, with a compound having the formula 7:

$$[CH_3SCH_2O(CHR^3)_q—]_3C—X^2—Z' \quad (7)$$

wherein Z' is the end group Z or another group to be replaced by the end group Z; and wherein if the group Z' is another group to be replaced by the end group Z, then group Z' is replaced by said end group Z, and wherein G'O is deprotected to obtain a compound having the residue GO.

18. A method according to claim 17, wherein the reaction of the compound of the formula 6:

$$G'O—(CHR^1)_n[O(CHR^2)_p]_rOH \quad (6)$$

with the compound of the formula 7:

$$[CH_3SCH_2O(CHR^3)_q—]_3C—X^2—Z' \quad (7)$$

is carried out in the presence of N-iodosuccinimide and trifluoromethanesulfonic acid.

19. A method according to claim 17, wherein the glycoside residue G'O is protected by hydroxyl-protecting benzoyl groups, which are later removed by treatment with potassium-tert butylate.

20. A method according to claim 17, wherein Z' is a protected reactive group which, after de-protection, is replaced by an end group Z selected from the group consisting of a lipophilic group, a drug residue, and a drug carrier residue.

21. Method of preparing a triantennary cluster glycoside of formula 8:

$$[GO—(CHR^1)_n[O(CHR^2)_p]_rOCH_2O(CHR^3)_q—]_3C—NH—X^3—Z \quad (8)$$

wherein GO— is a glycoside residue selected from the group consisting of monosaccharides and disaccharides;

wherein $X^3$ is an end group spacer about 4 atoms to about 12 atoms;

wherein Z is an end group selected from the group consisting of an optionally protected reactive group, a lipophilic group, a drug residue and a drug carrier residue, excluding a tetrakis-O-(3-carboxy-propionyl) pentaerythritol tetrakis-(1,2,3,4-tetra-O-benzyl-α-D-glucopyranosid-6-yl)tetraester, and a tetrakis-O-(3-carboxy-propionyl)pentaerythritol tetrakis-(α-D-glucopyranosid-6-yl)tetraester;

wherein $R^1$–$R^3$ is a hydrogen atom or an alkyl group having 1–4 carbon atoms;

wherein n, p and q is an integer from 1–6; and wherein r is an integer from 0–6;

said method of preparing said triantennary glycoside having the step of:

reacting formula 6:

$$G'O-(CHR^1)_n[O(CHR^2)_p]_r OH \qquad (6)$$

wherein G'O— is a residue of a protected glycoside selected from the group consisting of monosaccharides and disaccharides, with a compound of formula 9:

$$[CH_3SCH_2O(CHR^3)_q-]_3C-NHQ \qquad (9)$$

wherein Q is an amino-protecting group, thereby resulting in a compound having a free amino group for subsequent attachment of —$X^3$—Z to said free amino group to form a —NH—$X^3$—Z group, and wherein in the glycoside residue G'O is deprotected to obtain the glycoside residue GO.

22. A method according to claim 17, wherein the compound of the formula 6:

$$G'O-(CHR^1)_n[O(CHR^2)_p]_r OH \qquad (6)$$

is prepared by reacting a compound of the formula 10:

$$G'-SC_2H_5 \qquad (10)$$

with a compound of the formula 11:

$$HO(CHR^1)_n[O(CHR^2)_p]_r OH \qquad (11)$$

23. A method according to claim 22, wherein the reaction of the compound of the formula 10:

$$G'-SC_2H_5 \qquad (10)$$

with the compound of the formula 11

$$HO(CHR^1)_n[O(CHR^2)_p]_r OH \qquad (11)$$

is carried out in the presence of N-iodosuccinimide and trifluoromethanesulfonic acid.

\* \* \* \* \*

UNITED STATES PATENT AND TRADEMARK OFFICE
CERTIFICATE OF CORRECTION

PATENT NO. : 5,885,968
DATED : March 23, 1999
INVENTOR(S) : Biessen et al.

It is certified that error appears in the above-indentified patent and that said Letters Patent is hereby corrected as shown below:

In Column 7, Line 66, the patent now reads "$G'O\text{-}(CH^1R)_n[(CHR^2)_p]_rOH$"; this should read --$G'O\text{-}(CHR^1)_n[O(CHR^2)_p]_rOH$--.

In Column 8, Line 1, the patent now reads "$[CH_3SCH_2O(CHR^3)_q\text{-}]_3C\text{-}X^2Z'''$"; this should read --$[CH_3SCH_2O(CHR^3)_q\text{-}]_3C\text{-}X^2\text{-}Z'$--.

In Column 8, Line 11, the patent now reads "$[CH_3SCH_2O(CHR^3)_q\text{-}C\text{-}X^2\text{-}Z'''$"; this should read --$[CH_3SCH_2O(CHR^3)_q\text{-}]_3C\text{-}X^2\text{-}Z'$--.

In Column 8, Line 31, the patent now reads "wherein $G'$—"; this should read --wherein $G'O$— --.

In Column 10, Line 38, the patent now reads "$R=\ \text{—}O[C(CH_2)_2O]_2H)$"; this should read --$R=\ \text{—}O[(CH_2)_2O]_2H)$--.

In Column 14, Line 63, the patent now reads "$^1=\ \text{—}CO(CH_2)_4COOCH3)$"; this should read --$q^1=\ \text{—}CO(CH_2)_4COOCH_3)$--.

In Column 21, Line 17, the patent now reads "500 gl PBS"; this should read --500 $\mu$l PBS--.

UNITED STATES PATENT AND TRADEMARK OFFICE
CERTIFICATE OF CORRECTION

PATENT NO. : 5,885,968
DATED : March 23, 1999
INVENTOR(S) : Biessen et al.

It is certified that error appears in the above-indentified patent and that said Letters Patent is hereby corrected as shown below:

<u>In Column 25, Line 50,</u>      the patent now reads "(labeled with $^{125}$Å)"; this should read -- (labeled with $^{125}$I)--.

<u>In Column 28, Line 19,</u>      the patent now reads "Townsend, R.P.,"; this should read -- Townsend, R.R.,--.

Signed and Sealed this

Sixteenth Day of November, 1999

Attest:

Q. TODD DICKINSON

*Attesting Officer*      *Acting Commissioner of Patents and Trademarks*